(12) United States Patent
Dalen et al.

(10) Patent No.: US 11,967,426 B1
(45) Date of Patent: Apr. 23, 2024

(54) BATTERY AND WORKSTATION MONITORING SYSTEM AND DISPLAY

(71) Applicant: Enovate Medical, LLC, Murfreesboro, TN (US)

(72) Inventors: Mark Dalen, Murfreesboro, TN (US); Arlow Farrell, Murfreesboro, TN (US)

(73) Assignee: Enovate Medical, LLC, Murfreesboro, TN (US)

(*) Notice: Subject to any disclaimer, the term of this patent is extended or adjusted under 35 U.S.C. 154(b) by 0 days.

(21) Appl. No.: 17/929,930

(22) Filed: Sep. 6, 2022

Related U.S. Application Data

(63) Continuation of application No. 17/081,521, filed on Oct. 27, 2020, now Pat. No. 11,437,140, which is a continuation of application No. 15/898,583, filed on Feb. 17, 2018, now Pat. No. 10,818,392.

(60) Provisional application No. 62/628,623, filed on Feb. 9, 2018, provisional application No. 62/543,549, filed on Aug. 10, 2017.

(51) Int. Cl.
| | |
|---|---|
| G08B 21/00 | (2006.01) |
| G01R 31/382 | (2019.01) |
| G01R 31/396 | (2019.01) |
| G16H 40/40 | (2018.01) |
| G16H 40/67 | (2018.01) |

(52) U.S. Cl.
CPC ........... G16H 40/67 (2018.01); G01R 31/382 (2019.01); G01R 31/396 (2019.01); G16H 40/40 (2018.01)

(58) Field of Classification Search
CPC ...... G16H 40/67; G16H 40/40; G01R 31/382; G01R 31/396
USPC ........................................... 340/636.1
See application file for complete search history.

(56) References Cited

U.S. PATENT DOCUMENTS

| | | | |
|---|---|---|---|
| 10,318,001 B1* | 6/2019 | Spears ................ | H04W 4/021 |
| 2014/0266698 A1* | 9/2014 | Hall .................... | H04W 4/021 |
| | | | 340/539.13 |
| 2015/0134467 A1* | 5/2015 | Penilla ................ | B60L 50/66 |
| | | | 705/16 |
| 2015/0227127 A1* | 8/2015 | Miller ................. | G16H 20/13 |
| | | | 700/244 |
| 2015/0310180 A1* | 10/2015 | Pattekar ............. | G16H 40/20 |
| | | | 705/2 |
| 2016/0039295 A1* | 2/2016 | Madurai-Kumar ..... | B60L 53/64 |
| | | | 320/109 |

* cited by examiner

*Primary Examiner* — Mark S Rushing
(74) *Attorney, Agent, or Firm* — Holland & Knight, LLP; Matthew C. Cox

(57) ABSTRACT

An Asset Management System and a method for managing a fleet of assets is provided. The system is capable of determining use states and high-use periods of a fleet of mobile workstations. Use states are determined by sensors resident on mobile workstations, the sensors operable to detect the occurrence of a specified event. The Asset Management System is able to interpret data sent by the sensors and determine a type of use and use state for each mobile workstation based on the data or lack of data sent by the sensors. The Asset Management System is operable to determine periods of high-use across the fleet of mobile workstations. The Asset Management System is also operable to determine a return-on-investment level of each mobile workstation in the fleet and generate a heat map based on those levels.

18 Claims, 22 Drawing Sheets

FIG. 4

FIG. 17

BATTERY AND WORKSTATION MONITORING SYSTEM AND DISPLAY

CROSS-REFERENCES TO RELATED APPLICATIONS

This application is a continuation of U.S. patent application Ser. No. 17/081,521, filed Oct. 27, 2020, entitled BATTERY AND WORKSTATION MONITORING SYSTEM AND DISPLAY (now U.S. Pat. No. 11,437,140, issued on Sep. 6, 2022); which is a continuation of U.S. patent application Ser. No. 15/898,583, filed Feb. 17, 2018 entitled BATTERY AND WORKSTATION MONITORING SYSTEM AND DISPLAY (now U.S. Pat. No. 10,818,392, issued on Oct. 27, 2020); which claims priority to U.S. Provisional Patent No. 62/543,549, filed Aug. 10, 2017, entitled BATTERY AND WORKSTATION MONITORING SYSTEM AND DISPLAY and U.S. Provisional Patent No. 62/628,623, filed Feb. 9, 2018, entitled BATTERY AND WORKSTATION MONITORING SYSTEM AND DISPLAY. All of these applications are herein incorporated by reference in their entireties.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present subject matter relates generally to asset management and more particularly to the monitoring of a fleet of mobile workstations, battery use and health, and providing an effective user interface for tracking the use and health of the fleet.

In the current state of the art, hospitals and other health care providers use a variety of different assets to streamline and supplement the care that they provide to patients. However, the number of devices and the use of those devices is inherently difficult to track, including replacement dates and allocation across a facility. Devices may be spread and moved across a large facility, making it difficult to track location and keep an accurate inventory of the devices. Furthermore, the device management may be difficult as certain devices may need to be decommissioned or replaced after a certain time period.

Battery health representations include tabular displays of battery charge or battery health. Moreover, traditional battery capacity measurements calculate only the charge capacity of the initial charge, and do not adapt to subsequent usage or charging patterns. More particularly, a battery will have a different charge capacity during its first use and several subsequent uses as the charge capacity decreases over time. The battery is generally still healthy during the first several uses even though the charge capacity is decreasing. Many batteries are measured for health in comparison to the initial charge capacity.

Another inherent difficulty includes allocating the resources to the right people and departments without having unused devices or a deficiency of those devices in the facility. Use of medical carts or similar devices in hospitals is not distributed evenly across the 24-hour day, rendering traditional (average) measures of use ineffective. Many of these devices are critical to patient care, and must be available and locatable at any time.

Additionally, battery-powered devices in hospital settings frequently result in multiple failures or can repeatedly fail during use. These failures generally go unreported by clinicians, creating a backlog of non-functional units until there are sufficient failures within the fleet of devices as to negatively impact patient care.

Further problems in the present state of the art exist in the stated full-charge capacity of the battery. Specifically, present measurements of "full-charge" capacities are static, such that the capacity of a battery is rated at point-of-manufacture, point-of-sale, or point-of-first-use, and is not subsequently updated despite usage of the battery.

Previous attempts to monitor battery health and predict future battery outcomes have relied upon limited amounts of data (often taken from the battery's initial stages) or rely on direct measurements, such as voltage or temperatures outside of a predetermined range or specification. However, no solutions currently exist which base need for battery service on the use patterns of a fleet of devices to determine when a user can or should switch to another similar device.

Accordingly, there exists a need for a battery and workstation monitoring system which can manage, predict, and display the asset health of a plurality of devices within and across a fleet of similar devices.

BRIEF SUMMARY

The present disclosure generally provides systems and associated methods for managing a fleet of mobile workstations, a fleet of batteries, and the use and health of the workstations and batteries.

In some embodiments, the present disclosure provides a system for monitoring and tracking battery health relative to the capacity of a battery in charging and discharging. A charge sensor is in electrical communication with the battery such that the sensor detects the level of charge of a battery. The sensor generates a signal when a battery has discharged all of its power and generates a signal when it has reached maximum capacity during charging. The signal is sent to a transmitter which transmits a second signal to a processor, wherein the processor compares the discharge and full capacity charge data to average discharge and full capacity charge data and outputs a health of the battery. The processor then aggregates the health of a fleet of batteries and sends the data to a display.

In further embodiments, the present disclosure provides a system for monitoring usage and return on investment for a fleet of mobile workstations. The system comprises sensors for detecting use of a mobile workstation. The sensor is operable to measure energy output from batteries electrically coupled to the mobile work station. When a predetermined threshold of energy output is measured from the batteries, the mobile workstation is in use and the sensor generates an "in use" signal. A second sensor may be used for determining a user's proximity to the mobile work station. The second sensor detects when a user is located proximate the mobile work station, the sensor generates an "at the ready" signal. A third sensor may be used to detect when a mobile workstation is in transit. The third sensor may detect acceleration, location, or vibration. When a threshold input is reached in the third sensor, the sensor generates an "in transit" signal. The first, second, and third sensors may be electrically coupled to a transmitter which transmits the signals to a processor. The processor may receive the signals and aggregate the activity status of a fleet of mobile workstations. The processor may then determine periods of high activity and low activity. The processor may then compare the usage of each mobile workstation during periods of high activity to determine a return on investment (ROI) value for each mobile workstation. The processor may then generate a display signal which is transmitted to a display.

Additional objects, advantages, and novel features will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities, and combinations particularly pointed out in the appended claims.

BRIEF DESCRIPTION OF THE DRAWINGS

FIG. 4 is an exemplary embodiment of a battery inventory on a graphical user interface.

FIG. 17 is an exemplary embodiment of an asset drift report view on a graphical user interface.

DETAILED DESCRIPTION

Figure 1:
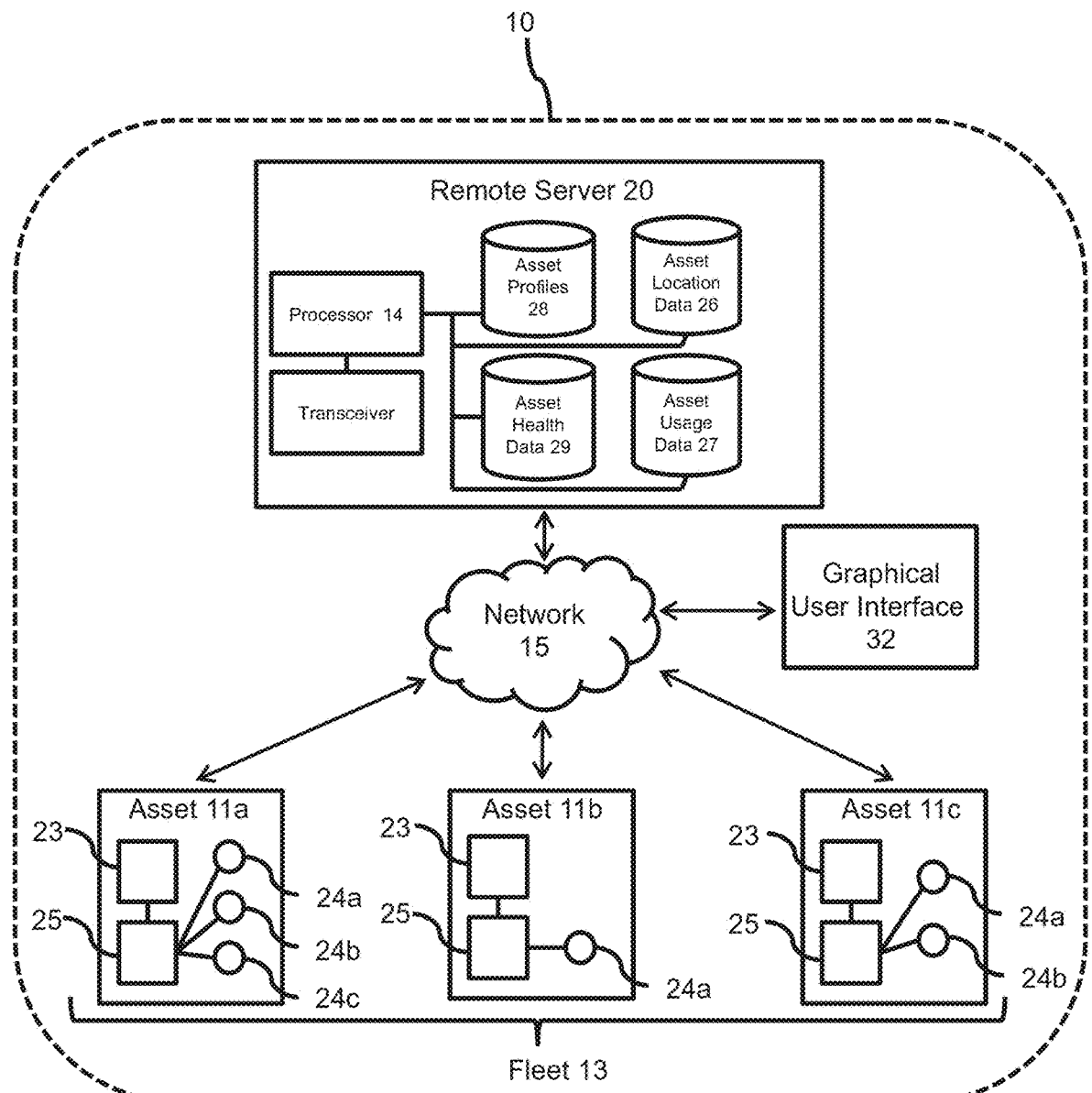
FIG. 1 is an exemplary embodiment of an asset management system.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing, or as otherwise described. A person of skill in the art will recognize that the apparatus can assume different orientations when in use.

To meet the needs described above and others, the present disclosure provides a battery and workplace monitoring system which can represent, manage, predict, and display the battery health of a plurality of devices within and across a fleet of similar devices or assets.

The battery and workstation monitoring system and display comprises various parts and features for allowing users to manage and track mobile workstations and batteries individually and as a fleet. A first aspect of the disclosure is a system for providing a heat map including charge levels of a fleet of batteries, health levels of a fleet of batteries, and a return on investment for a fleet of workstations. A second aspect of the disclosure is a Battery Predictive Report providing predicted dates when assets will fall below predetermined health thresholds. A third aspect of the disclosure is a Return on Investment report including fleet-wide and individual asset return of investment for a fleet of assets base on asset usage and peak usage intervals. A fourth aspect of the disclosure includes a Graphical User Interface for dynamically monitoring and managing a fleet of assets.

Heat Map

A first aspect of the disclosure provides an Asset Management System (AMS) 10 which provides a heat map format for monitoring and managing a fleet of assets. Referring to FIG. 1, the AMS 10 may comprise a remote server 20 operably linked to an asset 11 or a fleet 13 of assets via a network 15. The assets 11 may comprise a variety of devices including batteries, mobile workstations, medical equipment, mobile computers, tablets, phones, diagnostic equipment, and any other devices known to one of skill in the art.

A heat map 16 is a method for visually displaying data on a graphical user interface 32 for quick consumption and understanding. In some embodiments, a heat map 16 may display a series of symbols 18 in the form of rectangles, color-coded to reflect traits of a single asset 11 or a fleet 13 of assets. The information may be represented in many different forms including displaying the data by representing the health level of each of the batteries by shape, color, shading, density of markings, or any other method readily available and known to one of skill in the art. The heat map 16 may also be scalable and may have the ability to select different ranges of the fleet 13 of assets.

Each heat map 16 is populated with information based on specific inputs produced by the AMS 10 and received and processed at the remote server 20. Each heat map 16 may display specific dynamic outputs produced by the AMS 10, including charge levels of batteries in a fleet 13, current health levels of batteries in a fleet 13, or Return on Investment of a fleet 13 of assets.

Each battery may be represented by a single representation 18. In other embodiments, sub-groups of the fleet 13 may be represented by a single representation 18. In one embodiment, the fleet 13 of batteries (total fleet, or partial subset fleet based on use areas) may be monitored for battery health where the relative health information is presented in a heat map 16 format on a graphical user interface 32 or display.

The heat map 16 may include additional functionalities beyond just displaying information for consumption by a user. Many of these functionalities will be described in more detail with specific reference to applications and in specific examples, however, the disclosure of those functionalities is to be broadly applied to each variation of the heat map described herein or which would be known to one of skill in the art. It is to be understood that the following sections incorporate the disclosure of a heat map are to be applied specifically in the context of battery charge, battery health and predictive health, and workstation fleet Return on Investment.

Accurate Battery Charge Representation and Location

A second aspect of the disclosure describes a system and method of battery charge determination and representation. One embodiment describes a system and method of battery charge representation by the AMS 10. Battery charge may be displayed in a heat map format such that a fleet 13 of batteries may all be represented on the heat map 16 and the overall charge level and need for charging of an entire fleet may be quickly understood.

Figure 2:
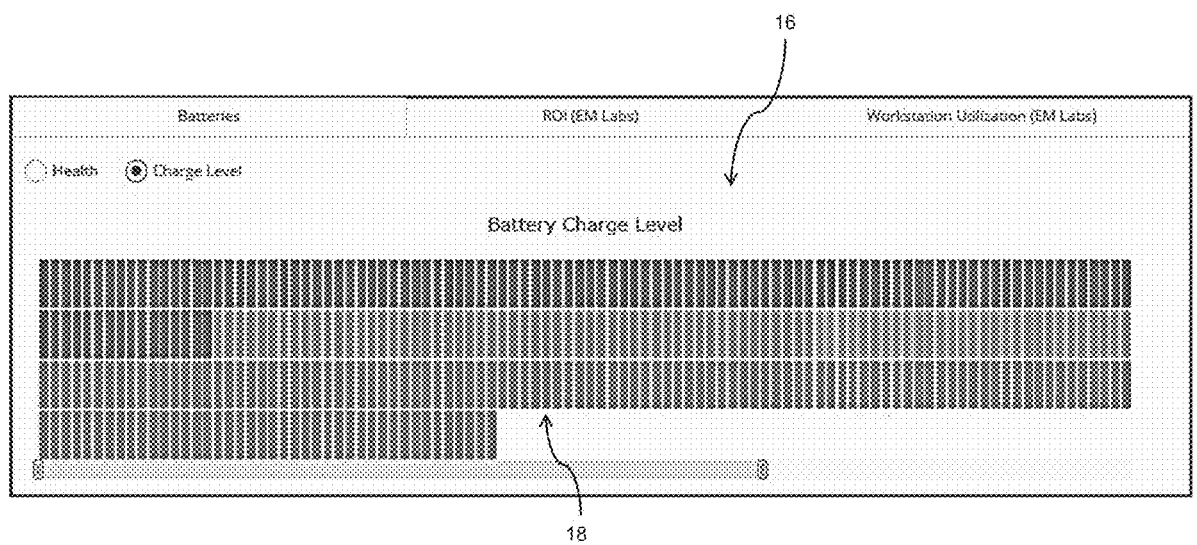
FIG. 2 is an exemplary embodiment of a heat map displaying the charge level of a fleet of assets.

Referring to FIG. 2, a heat map 16 may be implemented to display the charge levels of a fleet 13 of batteries (as a metric of the percent of current charge relative to the potential full charge or the most recent full charge capacity), wherein the heat map 16 provides alternative functionalities for managing the fleet 13 which are described herein.

A user may ascertain a variety of data relating to specific batteries and more broadly to specific assets 11 that might be represented on a heat map 16. The symbol 18 on the heat map 16 which represents a specific asset 11 may be selected to generate information relating to that asset, including location information. A Real-Time Location System (RTLS) 30 will presently be described and may be applied to each portion of this disclosure as will be described throughout.

Figure 3:
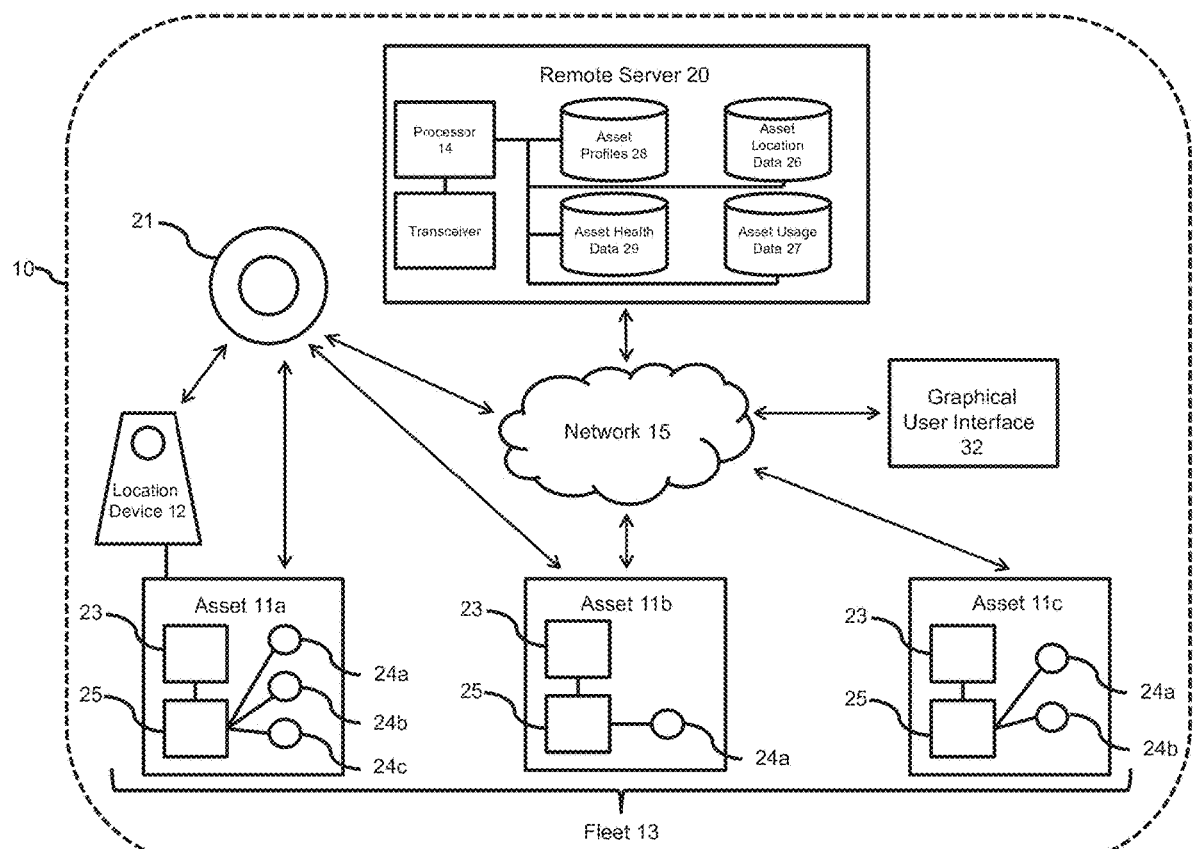
FIG. 3 is an exemplary embodiment of an asset management system using a beacon for real-time location services.

The RTLS 30 may be integrated into the AMS 10 and provides a system and method for tracking assets 11 across a fleet 13 of assets. Referring to FIG. 3, a first embodiment includes assets 11 and a fleet 13 of assets sending and receiving signals 22 to beacons 21 which relay information to the server 20 through a network 15. In some embodiments location devices 12 are deployed on each asset 11 and are operable to detect a signal 22 from the beacons 21. In some embodiments, the location device 12 may be operable to detect a signal 22 from another location device 12 or a beacon 21. The location device 12 is capable of determining a location within an area based on location principles such as triangulation based on the network of various location devices and beacons within the area. The beacons 21 are stationary and are configured to provide a static location for determining the location of assets 11 by the location devices 12 within a building, room, or area. The location of a first location device 12 may be determined by the RTLS 30 and may act as a temporary or ancillary beacon when the AMS 10 is unable to provide an accurate location of a second location device based on the signals sent and received from the stationary beacons 21. Location devices 12 may be operably coupled to an asset 11 or integrated into the circuitry of an asset 11.

Each location device 12 is associated with a specific asset 11. In one example, the location device 12 may be associated with a battery, a workstation, or any other device to be tracked within an area. Each asset 11 of the fleet 13 is assigned an asset profile 28 which is saved on a computer memory storage device of the AMS 10, which could be on a server 20. Each asset 11 of the fleet 13 of assets is assigned an asset location data 26 based on asset location data 26 associated with each asset 11. The asset location data 26 is associated with the asset profile 28. The asset profile 28 is updated periodically to reflect the most current location data associated with the asset. The updating of the asset profile 28 and the asset location data 26 of the asset 11 provides a dynamic view or snapshot of the location of a fleet 13 of assets within a system.

In some embodiments, the RTLS 30 may not be integrated in to the AMS 10, and the RTLS 30 may communicate the data to the AMS 10 via a network 15. The RTLS 30 may store a location device profile for each location device 12, and the AMS 10 may associate the data received for each location device 12 with the asset profile 28 to which the location device 12 is assigned. The RTLS 30 may specifically include battery location data and workstation location data.

Other data may be associated with each asset profile 28. In one example, a battery profile 28 on the server 20 may include charge level data, asset health data 29, asset usage data (or use state data) 27, manufacturer warranty data, any other information suitable and known to one of skill in the art. The AMS 10 is able to provide recommendations to users based on the information contained in the data of each of the asset profiles 28. In one example, if an asset 11 is a battery on a mobile workstation in a hospital and the battery is running low on charge, the asset management system 20 is capable of making a recommendation for locating a replacement battery nearby based on location data and charge level data of batteries in the AMS 10. The AMS 10 is able to determine the closest fully-charged or almost fully-charged batteries. The AMS 10 may be capable of filtering out those batteries that are in use on a different asset, for example, another mobile workstation based on location data, charge data, etc. In another example, the AMS 10 may recommend to a user where the nearest charging station or available charging terminal is located to place the discharged battery.

Because the AMS 10 is continuously updating the data associated with each asset profile 28, the AMS 10 is capable of providing dynamic recommendations for use of assets 11. For example, a user may be alerted that the charge level of a battery is running low while in a first room with a patient. The nearest charging station at that moment may be at a nurse station across the hall from the first room. The AMS 10 may recommend that a fully-charged battery be taken from the charging station at the nurse station and the discharged battery be placed on the same battery station for charging. However, the user may not be able to take the battery immediately to the charging station at the nurse station before visiting another patient on a different floor. Once the location data 32 associated with the battery is updated in the battery profile 28, the AMS 10 locates a second charging station which has an available fully-charged battery closest to the updated location of the mobile workstation. The AMS 10 then updates the recommendation to the user based on the new location data.

Figure 4:
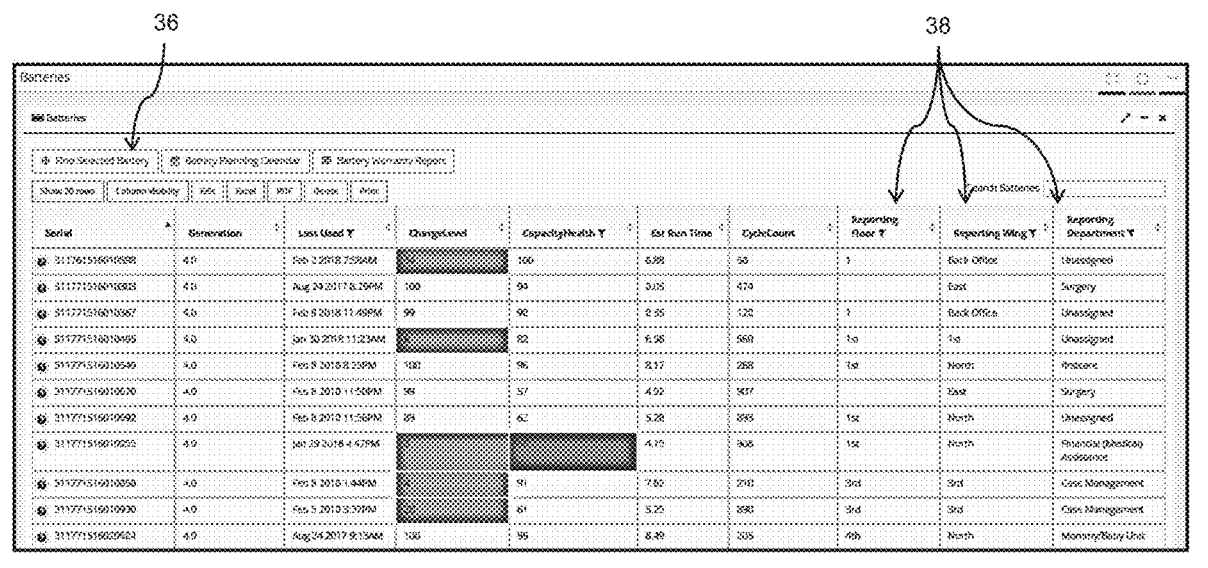
Figure 5:
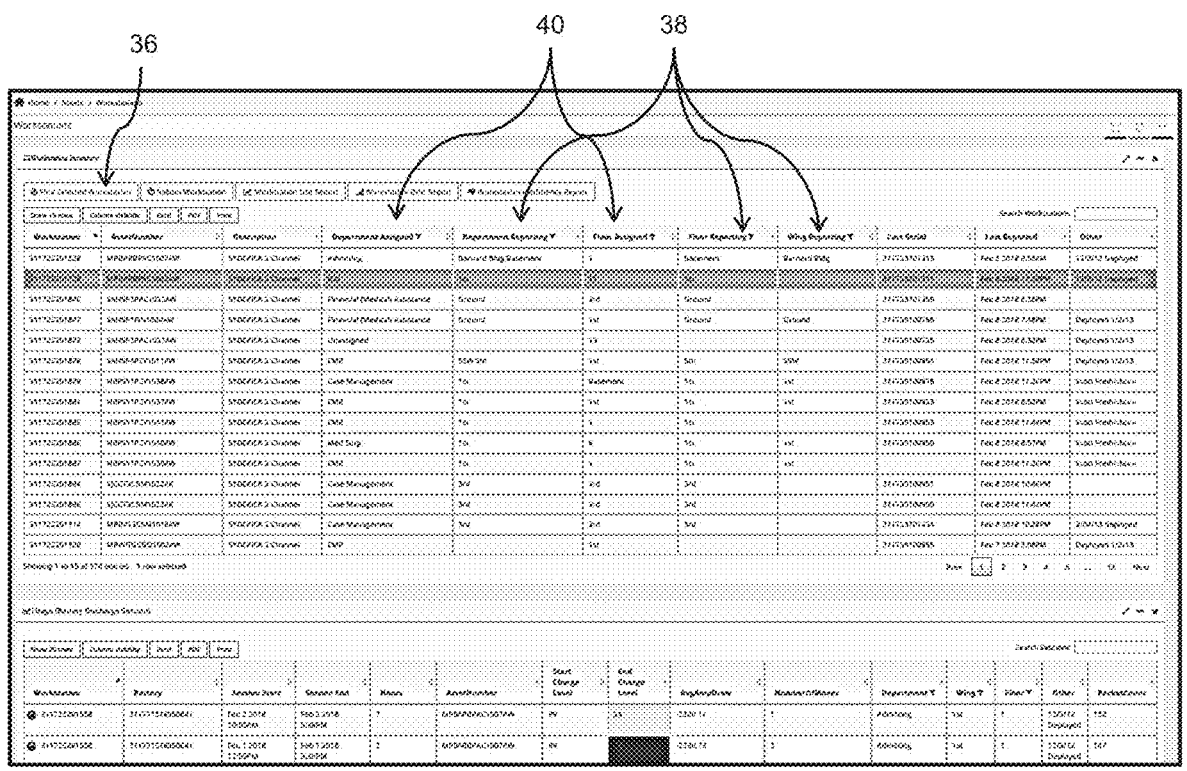
FIG. 5 is an exemplary embodiment of a workstation inventory on a graphical user interface.

The AMS 10 is also capable of providing reports of each asset 11 of the fleet 13 of assets. FIG. 4 and FIG. 5 demonstrate exemplary embodiments of workstation and battery inventories produced by the AMS 10. This includes an assigned location 38 of the asset 11 and the actual location 40 of the asset 11. For example, because mobile workstations are inherently moveable between locations, it may be difficult to track and keep an accurate inventory of the mobile workstations, even when designated for specific use in a specific location. In one example, a mobile workstation may be assigned specifically to a floor which houses an intensive care unit and a burn unit. A provider may be moving a patient from the intensive care unit to a transitional care unit on a different floor. The provider might take a cart that is technically assigned to the burn unit while seeing the patient in the intensive care unit and move the cart to the transitional care unit while transferring the patient. A user in the burn unit is able to access via a computer terminal the system to view the location of the mobile workstation that has been moved from the burn unit. A second user in the transitional care unit may notice that there is an excess number of carts in their unit and may access the system via a second computer terminal to determine the carts' locations and assigned locations. Thus each unit or department is able to maintain control of and access to inventory. The dynamic updating of location improves the system by providing users with the ability to quickly locate, return, or reallocate assets, and specifically inherently mobile assets, to the appropriate location within an area.

In some embodiments the real-time location system 30 and the other systems associated with this disclosure are a cloud-based system that monitors and manages mobile workstations and mobile assets with real-time visibility. In other embodiments, the system may be operable over a local network and server.

Current Battery Health Representation

A third aspect of the disclosure describes a system and method of variable battery health representation by the AMS 10. Asset health may be determined in a variety of situations specific to the asset 11 which is being managed. Generally, an AMS 10 requires a variety of sensors operably coupled to an asset 11 or a fleet 13 of assets for monitoring a number of factors indicative of health, such as temperature, flexion, tension, charge, etc. Asset health may be displayed in a heat map 16 and may be used in a variety of other interfaces and applications outside of a heat map format.

Battery health may be determined as a ratio of a Manufactured Full Charge Capacity (MFCC) and the currently available Full Charge Capacity (FCC). Specifically, the MFCC is the FCC of a battery at the time of manufacture. The ratio of the currently available FCC of a battery divided by the MFCC of the battery when the battery was first manufactured or new. The MFCC can be a set numeric value assigned by the manufacturer at the time of manufacture specifically. Each battery may be individually assessed to determine the specific battery's MFCC or the manufacturer may assign each battery with a MFCC based on the average of all similar battery models.

Alternatively, battery health may be determined as a ratio of the currently available Full Charge Capacity (FCC) divided by the Adjusted Full Charge Capacity (AFCC) of a battery. Separately, battery charge levels may be determined using similar factors, specifically, the battery charge level may be the ratio of the current charge level compared to a recent FCC, the MFCC, or the AFCC.

In one example, with a fleet of batteries, sensors 24 may be operably coupled to each battery and configured to sense when a battery has reached a FCC. A memory storage device may retain the FCC of the batteries so an asset processor 25 is able to retrieve that information to make a variety of determinations based on the previous FCC's of a battery. In another embodiment, the AMS 10 may store the FCC's over an initial period and the asset processor 25 may take the FCC's over the initial period to calculate an AFCC. The AFCC is the average maximum charge a battery will hold during its first 30 days use. This differs from the initial measurement of a brand-new battery, as this value varies during the first several charges, and the battery monitor system reports values that shift based on the initial charge levels and charge patterns. In other embodiments, the FCC and AFCC are calculated and stored on the remote server 20 and by the processor 14 of the remote server 20.

Figure 6:
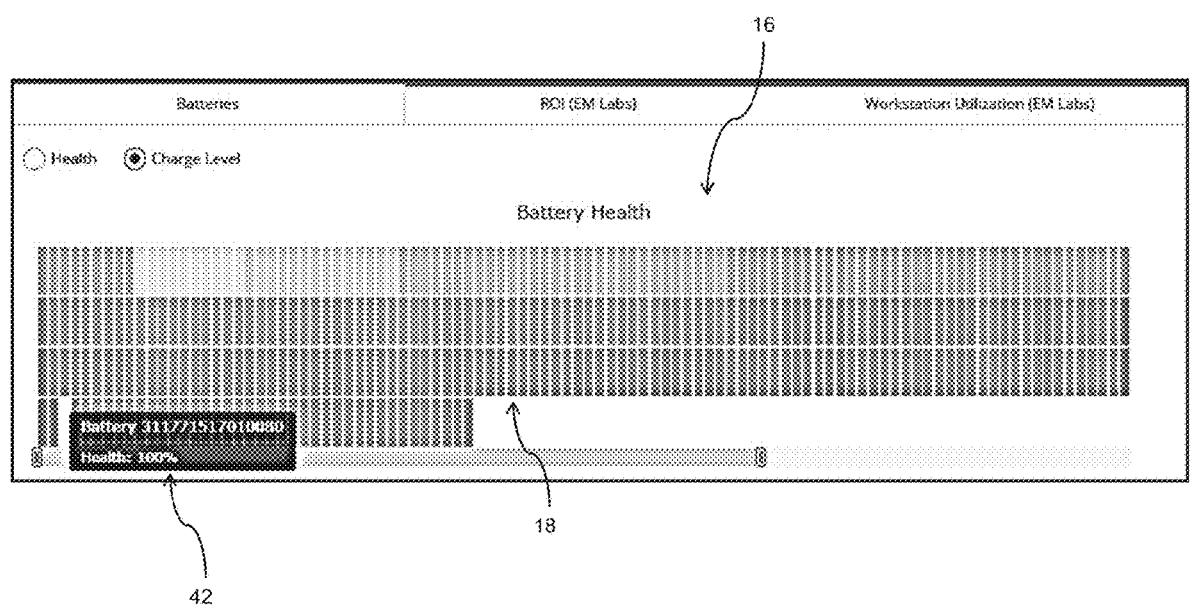
FIG. 6 is an exemplary embodiment of a heat map displaying the battery health level of a fleet of assets.

In one example, a user interface 32 may display battery health relating to each battery of a fleet of batteries. The user interface may include a heat map of the all of the batteries that have been profiled in the system, as shown in FIG. 6. A user may then select, via the user interface 32, a representation 18 of the battery which is displayed on the user interface. Once the selection has been made, in some embodiments, both the location data, any other data generated by sensors coupled to the assets, and any other data relating to the selected battery may be displayed on the user interface In one embodiment, battery health can be more accurately predicted by using the AFCC. AFCC provides a more accurate representation of a battery's charge capacity, because of the normal fluctuations in the FCC of a healthy battery during the initial uses of the battery. In some embodiments, the AFCC is the average charge a battery will hold during its first thirty (30) days of use. In other embodiments, the AFCC is the average charge a battery will hold over a variety of periods of time, including 1 week, 2 weeks, 3 weeks, 2 months, or any other acceptable period of time as may better predict a battery's FCC dependent on the specific properties of the given battery as one of ordinary skill in the art might determine. A battery charge capacity sensor is electrically coupled to the battery to measure the charge capacity of the battery. During the first thirty (30) days of use of the battery, the battery charge capacity sensor will determine the FCC of the battery when the battery is fully charged. The battery charge capacity sensor will generate a FCC signal containing the FCC data of the battery. A processor 14 will then receive the FCC data. In some embodiments, the processor 14 will then send the FCC data to a memory storage device. The storage device will collect the FCC data of a battery for the first thirty (30) days of the battery's use. The processor 14 will then retrieve the battery's FCC data and create an average of the FCC data, the average is then assigned to the battery as an AFCC for the battery. The battery's health is then determined by the ratio of the battery's current or most recent FCC to the AFCC that has been assigned to that battery. In some embodiments, the AFCC may be determined by determining the average FCC for a group of batteries over the first thirty (30) days of each battery's life. In other embodiments, the AFCC is determined by calculating the average FCC a fleet of batteries or subset of the fleet over the first thirty (30) days of each batteries life.

Figure 18:
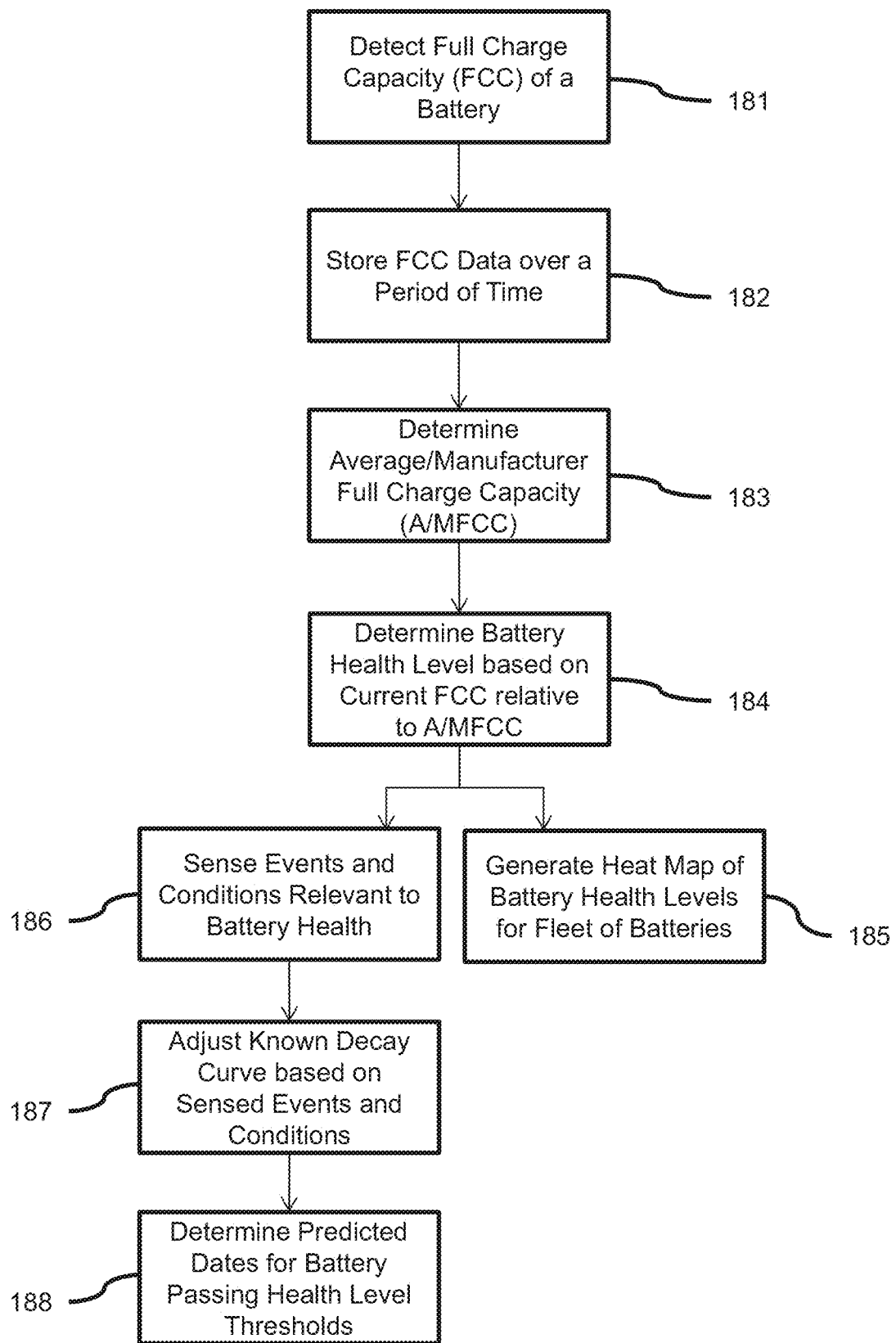
FIG. 18 is an exemplary embodiment of a method for determining and predicting battery health.

Referring again to FIG. 6, a heat map 16 may depict one aspect of the present disclosure. Specifically, FIG. 6 presents a means of variable battery health representation. Battery health is determined as a ratio of the currently available FCC divided by the MFCC or AFCC of a battery. As can be seen in FIG. 18, variable health representation may include "Detect Full Charge Capacity (FCC) of a Battery" 181, "Store FCC Data over a Period of Time" 182, "Determine Average/Manufacturer Full Charge Capacity (A/MFCC)" 183, "Determine Battery Health Level based on Current FCC relative to A/MFCC" 184, and "Generate Heat Map of Battery Health Levels for Fleet of Batteries" 185.

In an embodiment, the heat map 16 represents each battery within a fleet 13, with the current battery health expressed in a color, from green (best) to red (worst). Additionally, the heat map 16 includes a scroll and scale control to expand and collapse the map, or scroll to one side or the other, in order to view either the entire fleet 13 or pan and zoom to any portion of the heat map 16.

In one embodiment, a user may select a setting in which the battery health data may be displayed such that each symbol 18 representing a battery is arranged into a section according to its health relative to the other batteries in the fleet 13. This allows a user to quickly comprehend the overall health of the fleet 13. The user may further refine the data that is being displayed by selecting the battery by department. In one example, a hospital has many departments where batteries and mobile workstations are used including emergency departments, intensive care units, surgical centers, laboratories, cardiology departments, neurology departments, and all throughout a hospital including nursing stations, patient rooms, offices, and operating rooms. In one embodiment, each battery may be assigned to a specific department. In another embodiment, each battery may be tracked by location and be assigned to a department based on its location. This information and the assignments may be represented by data associated with the profile 28 of an asset 11 on the memory storage device of the AMS 10. As such, a user may select a setting on the AMS 10 to display the battery health based on the department to which it has been assigned or based on the location of the battery. Department designations may be used in any setting including warehouses, businesses, malls, etc.

In some embodiments, the heat map 16 may be interactive. In one embodiment, the heat map 16 may be scalable such that varying levels of data may be displayed on a single map. This allows a user to select a more detailed view of the battery health or a broader picture of the health of the fleet 13. In other embodiments, each symbol 18 representing the life of the battery may be selectable such that when the symbol 18 is selected, information regarding the specific battery that is represented by the symbol 18 is displayed. In one example, when a specific symbol 18 is selected, the AMS 10 may display the identity, location, length of life, make and model, last use, serial number, charge level, estimated run time, cycle count, warranty information, or any other information that is readily ascertainable by one of skill in the art.

In some embodiments, a FCC can be established for each battery. The target FCC may differ from the published FCC. For example, the charge that each battery will accept over its initial weeks of use is measured as well as the lowest charge level to which it can be discharged to establish a target FCC, which may differ from the published FCC. This establishes the target (or new battery) FCC for each individual battery, and the target FCC data may be stored on the memory storage device of the AMS 10 and associated with the profile 28 of that battery.

In other embodiments, the range over which the battery can be charged is continually monitored, wherein the current available energy that can be accessed between the current FCC and the level to which it can be discharged is measured. The ratio of current energy available or FCC divided by the "new battery" charge capacity available or target FCC is determined for each battery and that ratio, expressed as a percentage, is the battery health. Assets 11 can be filtered by department to see a subset of the data. Battery health data may be stored on the memory storage device of the AMS 10 and associated with the profile 28 of that battery.

In some embodiments the assets 11 may be a fleet 13 of batteries or a subset of the fleet 13 of batteries. A fleet 13 of batteries may be used in a variety of situations, including healthcare facilities, manufacturing facilities, malls, department stores, warehouses, etc. The AMS 10 is configured to provide real time analytics on the charge and health of the fleet 13 of batteries. In other embodiments, the AMS 10 can be used to track a variety of other assets 11, including computer stations, kiosks, tools, or any other device suitable and known to one of skill in the art.

In other embodiments the AMS 10 may include a variety of other components, such as memory storage devices, receivers, transmitters, transceivers, specialized sensors, internet capable components, or any other device suitable and known to one of skill in the art. A memory storage device may be configured to store a variety of asset conditions which are monitored by sensors. The memory storage device may be accessed by the processor 14 to determine certain metrics for which the AMS 10 is monitoring.

The sensors 24 are operably coupled to the system via a wired or wireless connection. The connection may occur over a network 15 such as a local area network (LAN), wide area network (WAN), virtual LAN (VLAN), virtual private network (VPN), or any other wireless protocol such as Bluetooth™ Low Energy (BLE), near field communication (NFC), or any other method suitable and known to one of skill in the art. The sensors send data via a transmitter or transceiver 23 when certain conditions are met by the asset to trigger a response from the sensor. The AMS 10, including a processor 14, then takes the data from the sensor and interprets the data and outputs analyzed data. The analyzed data may be operable to be displayed on a user interface to a user.

Predictive Health of Battery Assets

The next aspect of the disclosure relates to the predictive health of battery assets based on current health levels, battery decay curves, and a variety of predictive inputs which are measured and used in determining predicted health levels over future periods of time. Now referring to FIG. 7, predictive battery health may be calculated for a battery or a fleet 13 of batteries, which may be displayed on a predictive calendar 107.

As previously discussed, current battery health may be determined as a ratio of the current FCC divided by the AFCC of a battery. This determination allows for a predictive model for battery health such that, in an embodiment, 6-month and 12-month predictions (or any other increment of time) can be made to enable planning and organization of resources based on accurate, dynamic, data-driven models.

Battery health degradation is based on the known, published battery decay curves, adjusted for both the general degradation of the battery packs used, and degradation of the specific battery pack as opposed to degradation of the general battery packs, considered across the entire fleet. The decay curve may be periodically adjusted based on actual data collected from the fleet, the specific battery, and updates from the battery manufacturer.

In an embodiment, use of the battery pack is continually monitored and applied to the degradation curve to predict when the battery pack will hit certain health levels and is periodically updated based on changes in use and other factors as determined by sensors 24 operably coupled to the batteries.

In some embodiments, the AMS 10 may determine the battery health degradation based on the known, published battery decay curves, adjusted for both the general degradation of the battery packs used, and degradation of the specific battery pack as opposed to degradation of the general battery packs, considered across the entire fleet 13. The curve is periodically adjusted based on actual data collected from the fleet 13 via the sensors 24 on each battery and updates from the battery manufacturer. The processor 14 receives the data generated by the sensors 24 on the battery and integrates that data into the degradation curves and any other data that may be used to update the model for predictive health of a battery. This provides an up-to-date or current representation of the health with its predictive health in such a way that a user may accurately anticipate the need for replacement, repair, or for general asset control purposes. In one embodiment, the decay curve is used to predict a dates at which the batteries will fall below a specific health threshold using full charge capacity readings, usage patterns such as starting charge, depth of discharge, and ending charge level, and cell imbalances using voltages and/or impedance of cells and/or groups of cells.

In some embodiments, the use of the battery pack is continually monitored and dynamically applied to the decay curve to predict when the battery pack will hit certain health levels. This application of the degradation curve is periodically updated based on changes in use. Changes in use may vary, but include and are not limited to discharging a fully charged battery versus discharging a partially charged battery, completely discharging a battery versus only partially discharging a battery prior to recharging, or power demands on the battery.

In other embodiments, each battery has an associated predictive degradation curve, which may be expressed in either a formula or table. The curve is based on age of the cells, number of cycles used, and rolling average current draw while discharging. This curve is generated by providing a baseline with the curve provided by historical performance of the fleet, adjusting the curve for ongoing field experience, and adjusting each battery curve, individually, for the fit of that battery to the curve based on the above cited three (3) factors.

Figure 7:
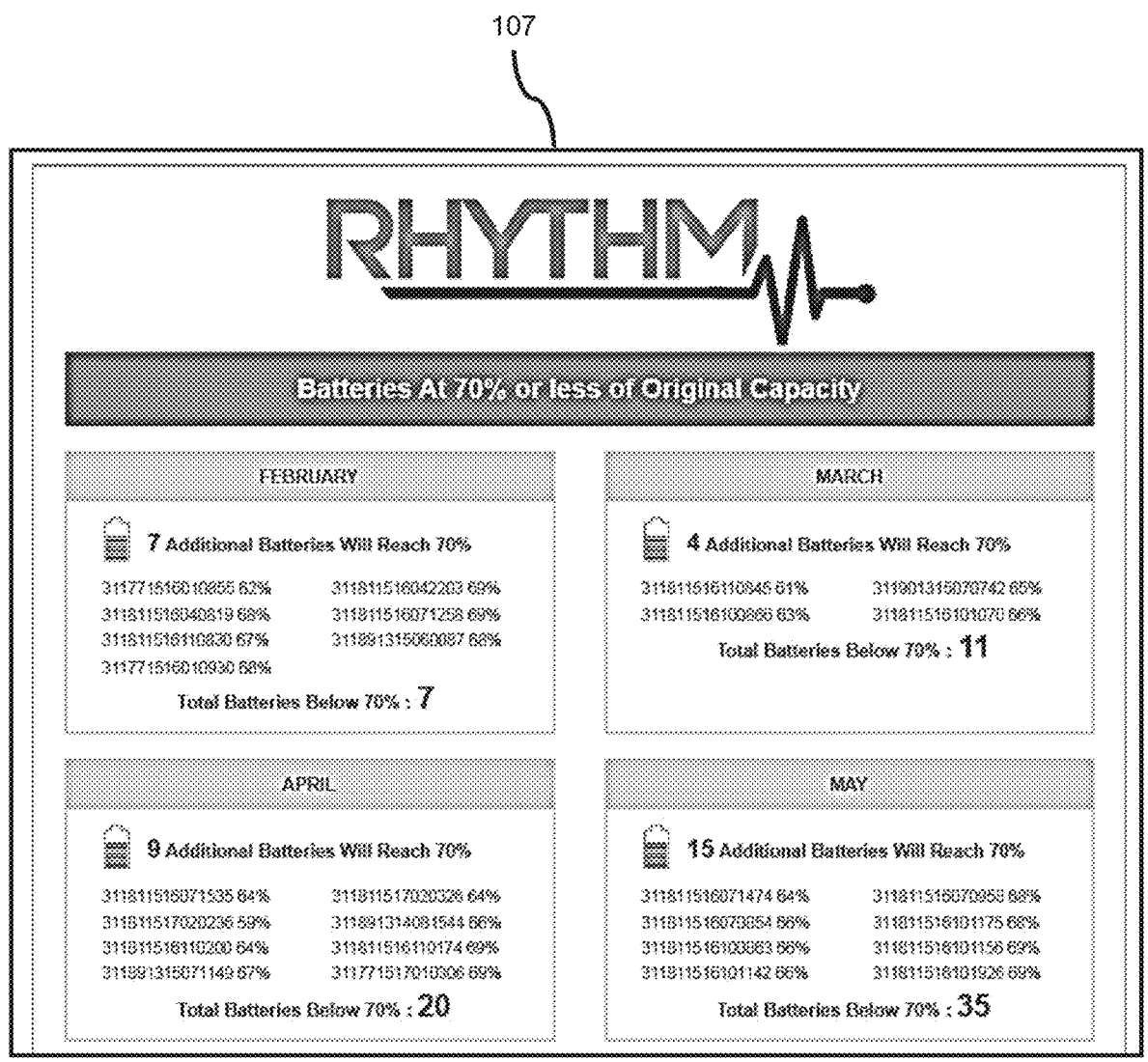
FIG. 7 is an exemplary embodiment of a predictive calendar for predicted health levels of a fleet of batteries.

Based on the rate of usage, age, and current draw, the system assigns a predicted time or time range in which each battery will reach various health levels. When the predicted health of a battery, based on the metrics described above, drops below a set percentage of battery health, the battery is added to a report tabulating those batteries which may need maintenance and/or replacement, and the expected date it would hit the threshold. The system allows for preemptive determination of battery wear and fleet size, without the problems described in the current state of the art, above. FIG. 7 demonstrates an exemplary embodiment of a calendar listing dates by which batteries are predicted to reach or pass a certain threshold of battery health.

Any number of metrics may be used to provide a more accurate predictive health of an battery and may not be limited to only type of use, age of battery, cycle count, battery error codes and faults, battery temperature, depth of discharge, ending charge, cell imbalances, voltages and/or impedances of battery cells or groups of cells, and any other data point that would be used by one of skill in the art. The AMS 10 described for monitoring and predicting health of the battery provides not only a display of these metrics and data points, but the AMS 10 provides accurate representations of potential fail timelines, predictions for replacement dates based on efficiencies, and predicted health thresholds for a future date. Prediction of battery life and life cycle is difficult, especially in a system where a fleet of batteries is used and can be used in a wide variety of different ways including quick discharges, partial discharges, varying operating environments including temperature, and many other variable settings and ways in which a battery may be implemented. The AMS 10 provides for a dynamically and accurately updated prediction of battery health and battery life thresholds. See FIG. 18 for a general overview.

The AMS 10 takes device specific information from a battery and applies it to a known degradation patterns to yield predictive health data. Thus, the prediction is based on data specific to the battery which the AMS 10 is evaluating separately because each battery may be experiencing varying use patterns and conditions. The system may also provide for the integration of data across several devices that share similar characteristics or circumstances of use to create an average predictive health for a battery, a sub-fleet, or a fleet of batteries, which may be practical for certain units or departments which use the same devices under similar circumstances and conditions. This allows situation specific predictions of battery health levels over time yielding unique and accurate timelines for each battery in the fleet of batteries.

In some embodiments, any data that is stored on a battery or stored regarding a battery from sensors 24 on or near a battery may be used as an input into the decay curve to predict a future health of the battery. Thus, data is not merely stored and presented to a user, but the AMS 10 is predicting outcomes and may provide recommendations based on the predicted outcomes. Such recommendations may include replacement dates, reallocation of batteries, and replacement of types of batteries with a second type of batteries that are better suited for a specific use.

In one embodiment, the AMS 10 includes a plurality of assets, a plurality of sensors 24, each sensor of the plurality of sensors coupled to separate assets 11 of the fleet 11 of assets, the plurality of sensors 24 operable to sense an asset condition and generate a signal at each instance when the asset condition is met across the plurality of assets. Alternatively, multiple sensors 24 of the plurality of sensors may be coupled to each asset 11 of the fleet 13 of assets. A processor 14 is operable to receive the signal and a secondary signal, wherein the secondary signal comprises a decay curve representing a predicted health life of each asset of the plurality of assets 11 and wherein the processor 14 is operable to integrate the asset condition 29 into the decay curve and generate an updated predicted health of each of the assets of the plurality of assets. A display is operable to display the updated predicted health of each of the assets 11 of the fleet 13 of assets In some embodiments, the processor 14 is resident on the AMS 10, and in another embodiment, the asset processor 25 is resident on each of the assets 11, to produce the predicted health of each asset. In the preferred embodiment, the AMS 10 is operable to receive all of the information, including the asset conditions, the data from the sensors, and the decay curves and use all of this data to produce a predicted health for each asset which can be associated with the asset profile 28 of the AMS 10. Each asset 11 may be operable to relay information to the AMS 10 via a network 15, including the data generated by the sensors 24 and other data relating to asset conditions and specifications. The sensors 24 may include cycle counters, voltmeters, ammeters, thermometers, and any other sensor known to one of skill in the art.

In another embodiment, a method of managing, monitoring, and allocating assets 11 in a facility includes detecting an asset condition via sensors 24 coupled to each asset 11 of a plurality of assets and operable to detect when the asset condition is met. The method includes generating a signal based the asset condition being satisfied, transmitting the signal to a processor 14, aggregating a plurality of signals via the processor 14, assigning a plurality of visual representation data to each of the plurality of signals, arranging the plurality of visual representation data based on the asset condition of the plurality of assets, and displaying the visual representation data on a display.

Predictive health can be presented in a heat map format, report, or other forms, using various forward-looking representations for the prediction of the battery health and life. In one embodiment, battery health percentage is represented on a heat map. "Red" batteries are below that cut off percentage of minimum battery health, with "green" down to "orange" showing how close each battery is to recommended replacement time, with orange-shaded cells closer to recommended replacement than green. Other methods for displaying the data may be implemented as previously discussed.

Figure 8:
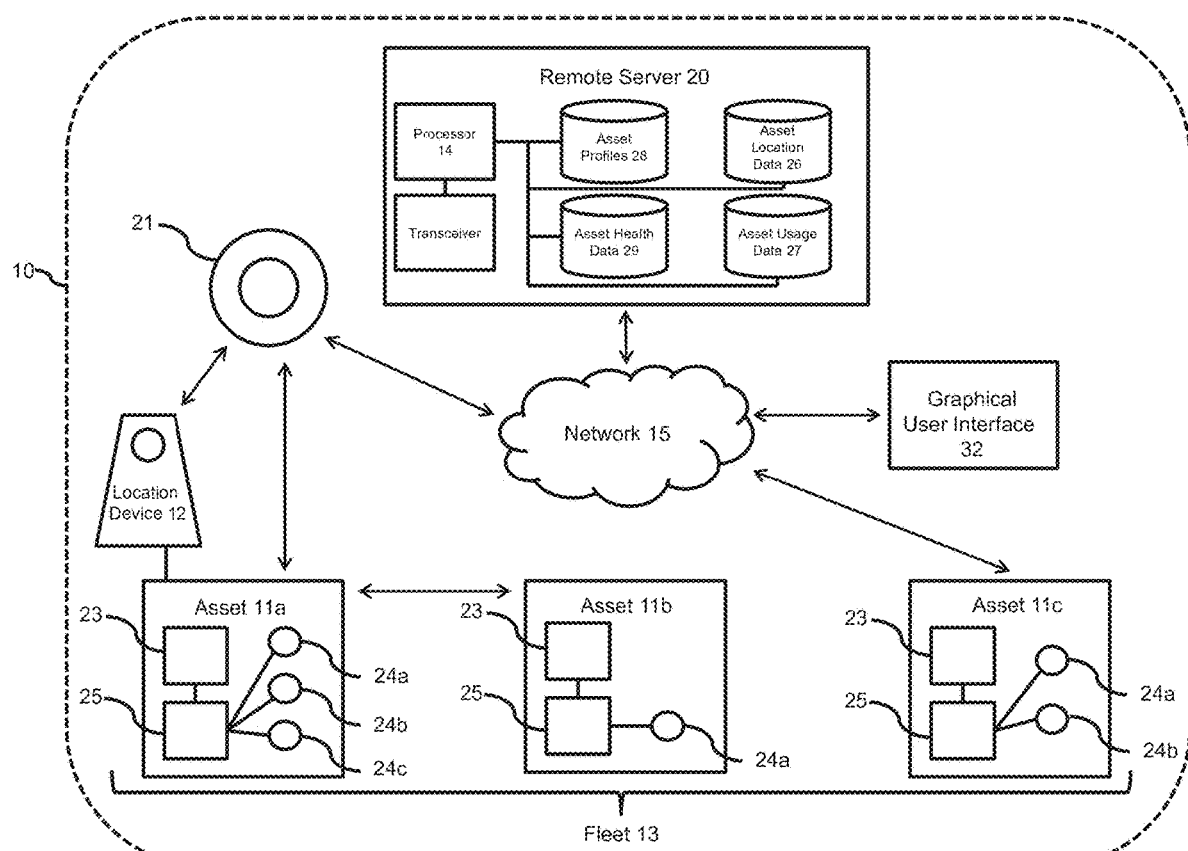
FIG. 8 is an exemplary embodiment of an asset management system wherein a battery communicates with the network via a second asset.

In some embodiments, data collected and stored relating to each battery may be relayed to the server 20 when the battery 11b is docked in a charging station or is in use on a mobile workstation. The data may be transferred via the existing communication networks provided by the charging stations and mobile workstations. See FIG. 8.

As can be seen in FIG. 18, predictive battery health may include "Detect Full Charge Capacity (FCC) of a Battery" 181, "Store FCC Data over a Period of Time" 182, "Determine Average/Manufacturer Full Charge Capacity (NMFCC)" 183, "Determine Battery Health Level based on Current FCC relative to A/MFCC" 184, "Generate Heat Map of Battery Health Levels for Fleet of Batteries" 185, "Sense Events and Conditions Relevant to Battery Health" 186, "Adjust Known Decay Curve based on Sensed Events and Conditions" 187, and "Determine Predicted Dates for Battery Passing Health Level Thresholds" 188.

In a possible embodiment, the heat map 16 can also be used as a visual predictive model to determine how many units within a fleet 13 may need replacing at a given time interval in the future. In one example, radio buttons and/or sliders adjust the time perspective of the heat map, from the present time into the future. Selection of a 6-month prediction, for example, would show the prediction of the health heat map 6 months from the current date based on the previously described determinations.

In some embodiments, a method for managing a plurality of batteries and predicting battery health of the plurality of batteries in a facility is also provided. The method may comprise determining a full charge capacity of a battery over an initial period of use, wherein the full charge capacity is determined each time the battery is fully charged, generating data comprising the full charge capacity of the battery for each time the battery is fully charged over the initial period of use, transmitting the data to a processor 14, determining by a processor 14 an average full charge capacity of the battery based on an average of the data, determining a current health level of the battery by dividing a current full charge capacity by the average full charge capacity, receiving a battery health decay curve, integrating the current health level of the battery into battery health decay curve, and generating a predictive decay curve.

Return on Investment of a Fleet

Figure 19:
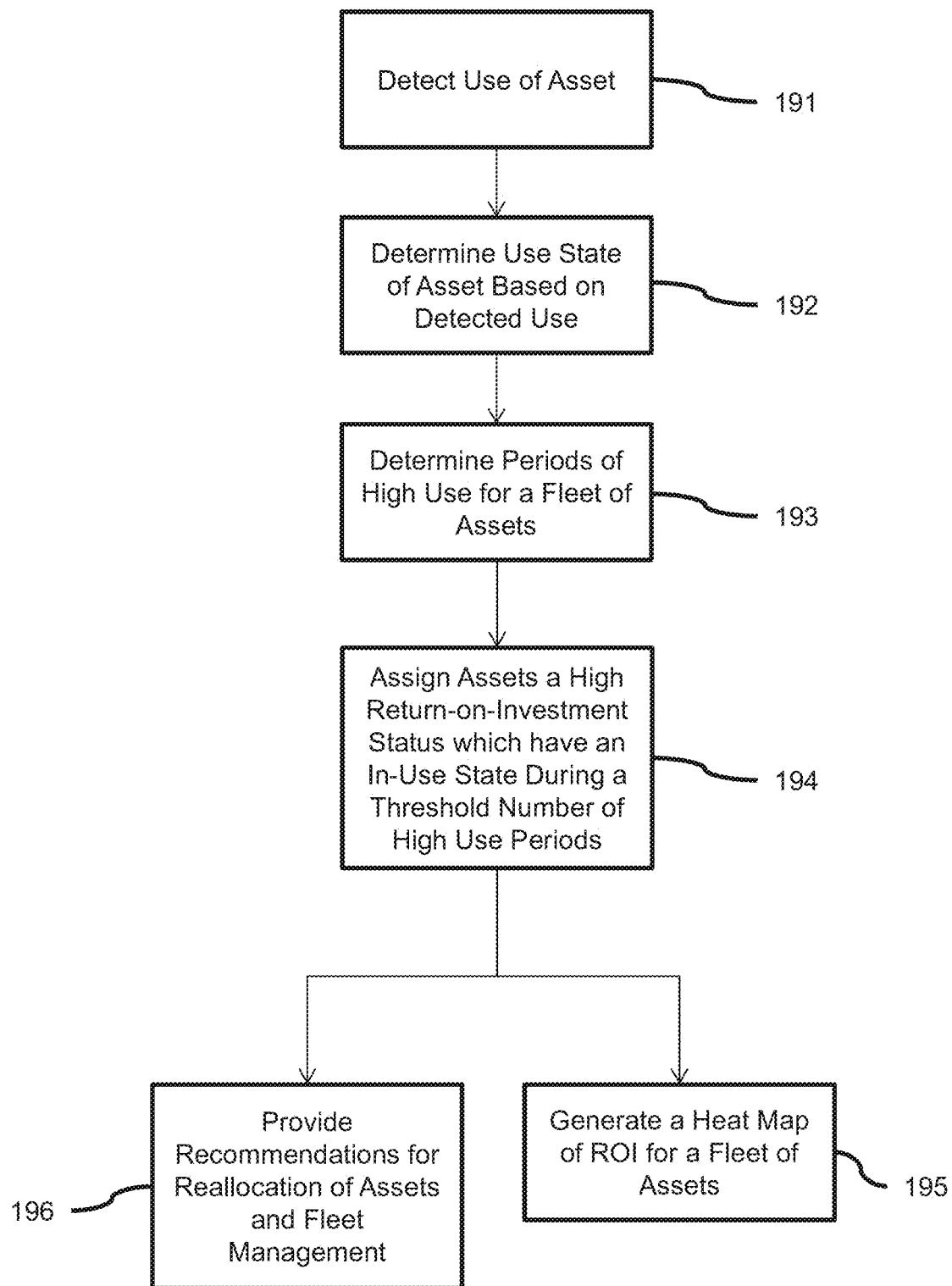
FIG. 19 is an exemplary embodiment of a method for determining use states and return on investment of an asset.

The next aspect of this disclosure relates to determining the return on investment ("ROI") of individual assets 11 or a fleet 13 of assets based on usage and usage patterns. The ROI portion of the present disclosure provides users with information relating to the use of an asset 11 during defined periods of time for consumption by the user as well as recommendations for allocation and use of assets 11 in a facility. ROI as presently disclosed provides the usage of an asset 11 during hours in which a fleet 13 of assets are being heavily used and not just an average use of the asset 11 over a day or month, thus providing a more accurate picture of the needs for assets and allocation of assets to meet those needs within a facility. Included in the disclosure is a novel system and method for determining when an asset 11 is in use and not in use. As can be seen in FIG. 19, one embodiment of determining ROI can include the steps of: "Detect Use of Asset" 191, "Determine Use State of Asset Based on Detected Use" 192, "Determine Periods of High Use for a Fleet of Assets" 193, "Assign Assets a High Return-on-Investment Status which have an In-Use State During a Threshold Number of High Use Periods" 194, and "Generate a Heat Map of ROI for a Fleet of Assets" 195. The AMS 10 is also operable to provide recommendations as shown in FIG. 19 as: "Detect Use of Asset" 191, "Determine Use State of Asset Based on Detected Use" 192, "Determine Periods of High Use for a Fleet of Assets" 193, "Assign Assets a High Return-on-Investment Status which have an In-Use State During a Threshold Number of High Use Periods" 194, and "Provide Recommendations for Reallocation of Assets and Fleet Management" 196.

ROI can be measured over any period (such as daily, 7-day, 14-day or any other suitable measurement period). Within those parameters, any asset 11 that is in use in any of the "High Use Periods" is flagged as "High ROI". Thus, ROI is the percentage of how many "High Use Periods" in which a given asset 11 (or group of assets) is used as a ratio of the total number of "High Use Periods" in the measured timeframe. ROI allows a user to determine, using data driven models which are powered by dynamic updating of asset use, if the assets 11 are being used effectively, how to reallocate resource for more effective use, and when adjustments need to be made within a fleet including supplementing the fleet with additional assets.

For each mobile workstation and battery, an ROI determination is continually performed. This is based on the use during a given period, compared to a target usage as represented by a fully used asset during peak periods of a day.

Certain assets 11 can be designated as HIGH ROI based on their intended use in a facility (e.g. Emergency Room, OR, etc.). Each day can be measured hour-by-hour to determine if a given asset is in use during each hour or not. Peak usage hours can be established for each department, based on the maximum assets in use for each hour of the day.

When a workstation is in use during peak usage hours, then it is flagged as HIGH ROI. Batteries are flagged as HIGH ROI if they are used during peak usage hours, or used in a workstation anytime within the next 24 hours.

In another embodiment, a user may manually profile a department for peak usage hours based on specific needs associated with the department. For example, the emergency room may profile a specific day of the week such as Saturday as a peak usage of assets 11. In other embodiments, the processor 14 is able to analyze the usage data associated with each asset profile 28 to determine when assets 11 are being utilized and determine the peak usage hours based on the actual use as read by sensors 24 operably coupled to each of the assets 11.

Over the course of time, each asset is given a rolling average ROI based on how many days it is flagged as HIGH ROI as opposed to days not flagged as HIGH ROI. In one embodiment, assets are color-coded into a chart or graph showing the ROI over user-selectable time frames (day, week, 14 days, etc.—up to 12 months).

In an embodiment, device use states can be defined as either "directly in use", "at the ready", "under the control of a clinician" (not available for someone else to use), "in-transit between use points" (for mobile devices), or "not in use". Such classifications enable indirect monitoring of the fleet.

Use states may be determined via various sensors 24 coupled to an asset 11. The sensors 24 may include voltmeters, ammeters, power consumption meters, accelerometers, 3-axis gyroscopes, 6-axis gyroscopes, magnetometers, key stroke monitors, vibration sensors, proximity sensors, NFC readers, RFID readers, and any other sensors known to one of skill in the art. The use of these some of the these sensors will be described in further detail below for determining how a use state of an asset 11 may be determined based on the data generated by each sensor in response to an condition being met.

Figure 20:
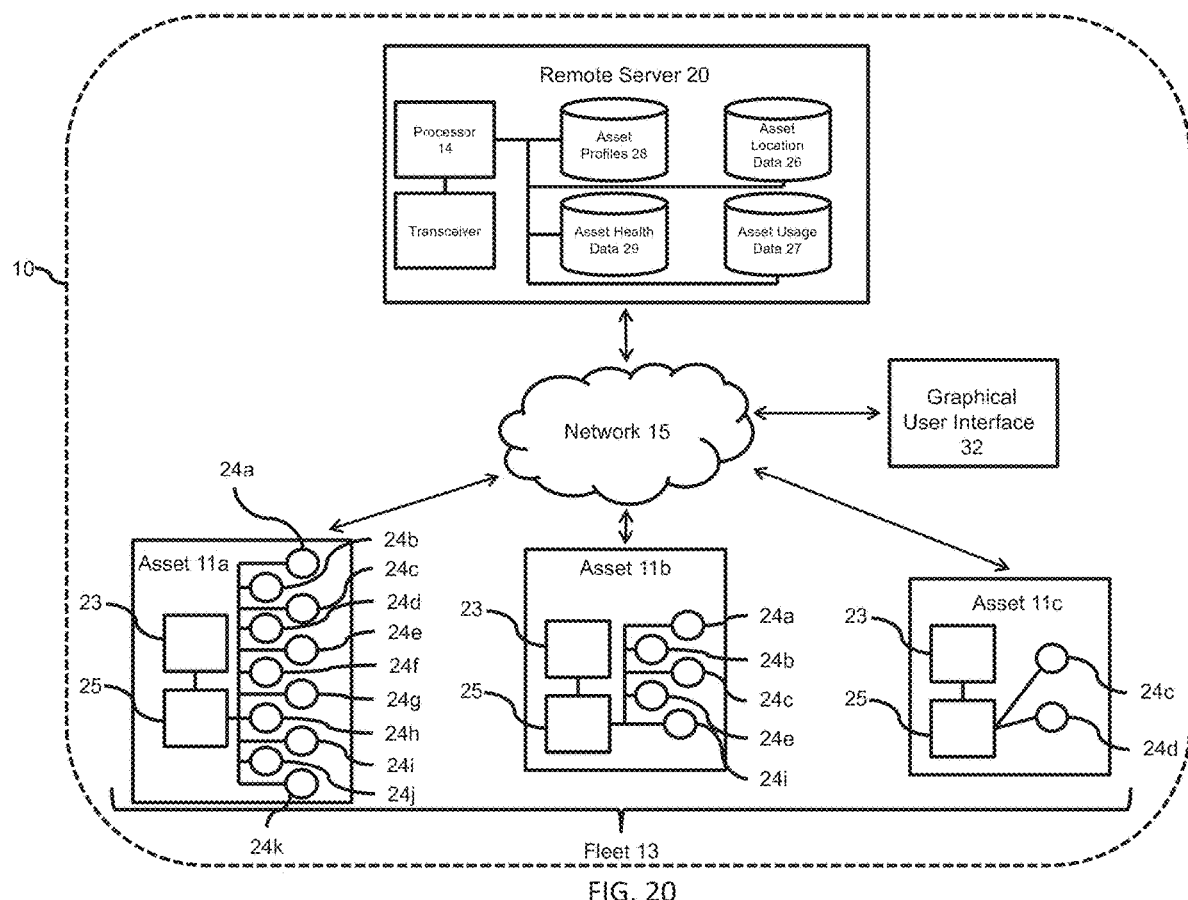
FIG. 20 is a first exemplary embodiment of an asset management system having assets with varying sensor arrays resident on assets.

Specifically, certain embodiments may include a variety of configurations of sensors 24 for determining the use state of an asset 11. In one embodiment as shown in FIG. 20, an asset 11a may be equipped with a voltmeter 24a, an ammeter 24b, a power consumption meter 24c, an accelerometer 24d, a 6-axis gyroscope 24e, a magnetometer 24f, a key stroke monitor 24g, a vibration sensor 24h, a proximity sensor 24i, an NFC reader 24j, and an RFID reader 24k, wherein each sensor 24 is operable to determine when conditions occur involving certain uses of the asset and to communicate those events to the AMS 10. A second asset 11b may be equipped with a voltmeter 24a, an ammeter 24b, a power consumption meter 24c, a 6-axis gyroscope 24e, and a proximity sensor 24i, wherein each sensor 24 is operable to determine when conditions occur involving certain uses of the asset and to communicate those events to the AMS 10. A third asset 11a may be equipped with a power consumption meter 24c and an accelerometer 24d, wherein each sensor 24 is operable to determine when conditions occur involving certain uses of the asset and to communicate those events to the AMS 10. It is within the scope of this disclosure that any asset may be a combination of these sensors 24 may be present on an asset, however, several other variations of sensors 24 on an asset 11 will be specifically mentioned in the following examples.

Figure 21:
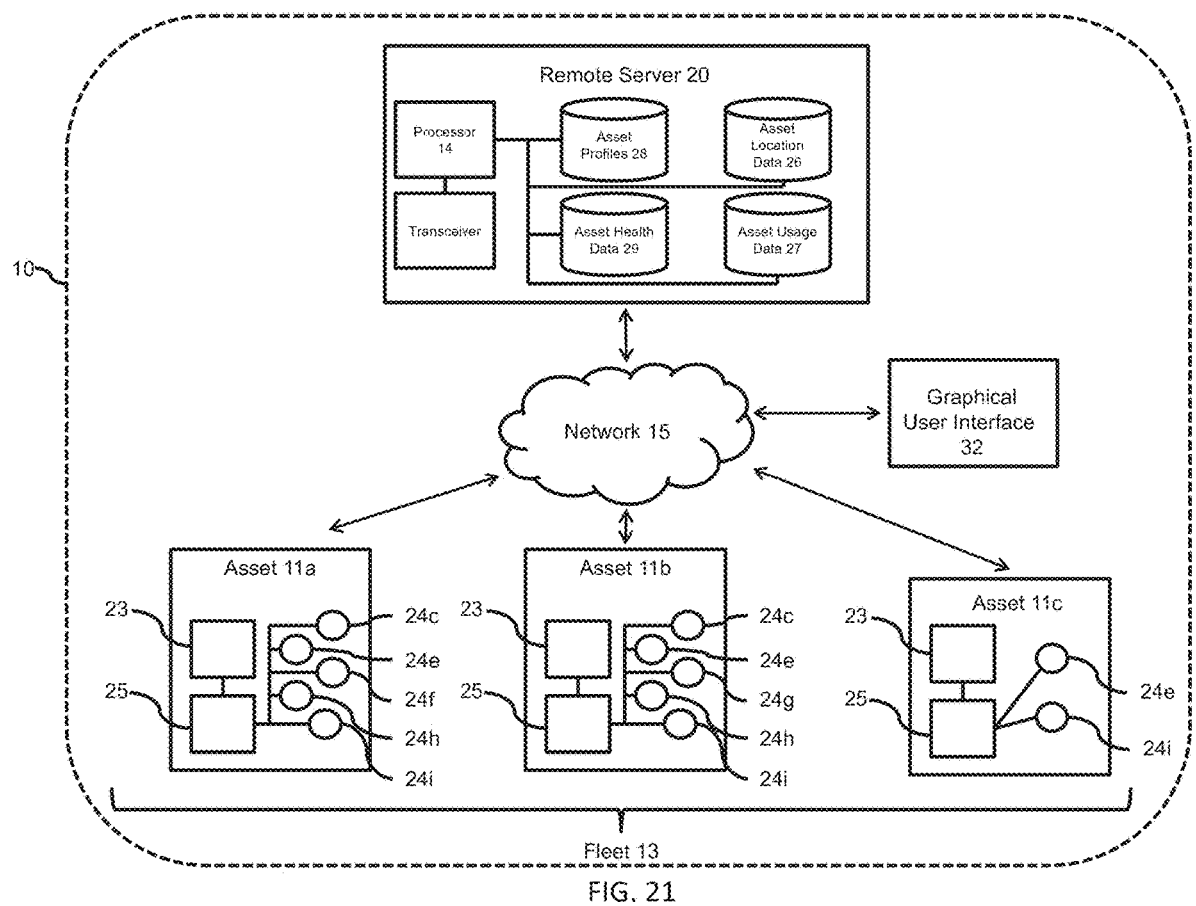
FIG. 21 is a second exemplary embodiment of an asset management system having assets with varying sensor arrays resident on assets.

In another embodiment as shown in FIG. 21, an asset 11a may be equipped with a power consumption meter 24c, a 6-axis gyroscope 24e, a magnetometer 24f, a vibration sensor 24h, and a proximity sensor 24i, wherein each sensor 24 is operable to determine when conditions occur involving certain uses of the asset and to communicate those events to the AMS 10. A second asset 11b may be equipped with a power consumption meter 24c, a 6-axis gyroscope 24e, a key stroke monitor 24g, a vibration sensor 24h, and a proximity sensor 24i, wherein each sensor 24 is operable to determine when conditions occur involving certain uses of the asset and to communicate those events to the AMS 10. A third asset 11a may be equipped with a 6-axis gyroscope 24e and a proximity sensor 24i, wherein each sensor 24 is operable to determine when conditions occur involving certain uses of the asset and to communicate those events to the AMS 10.

Figure 22:
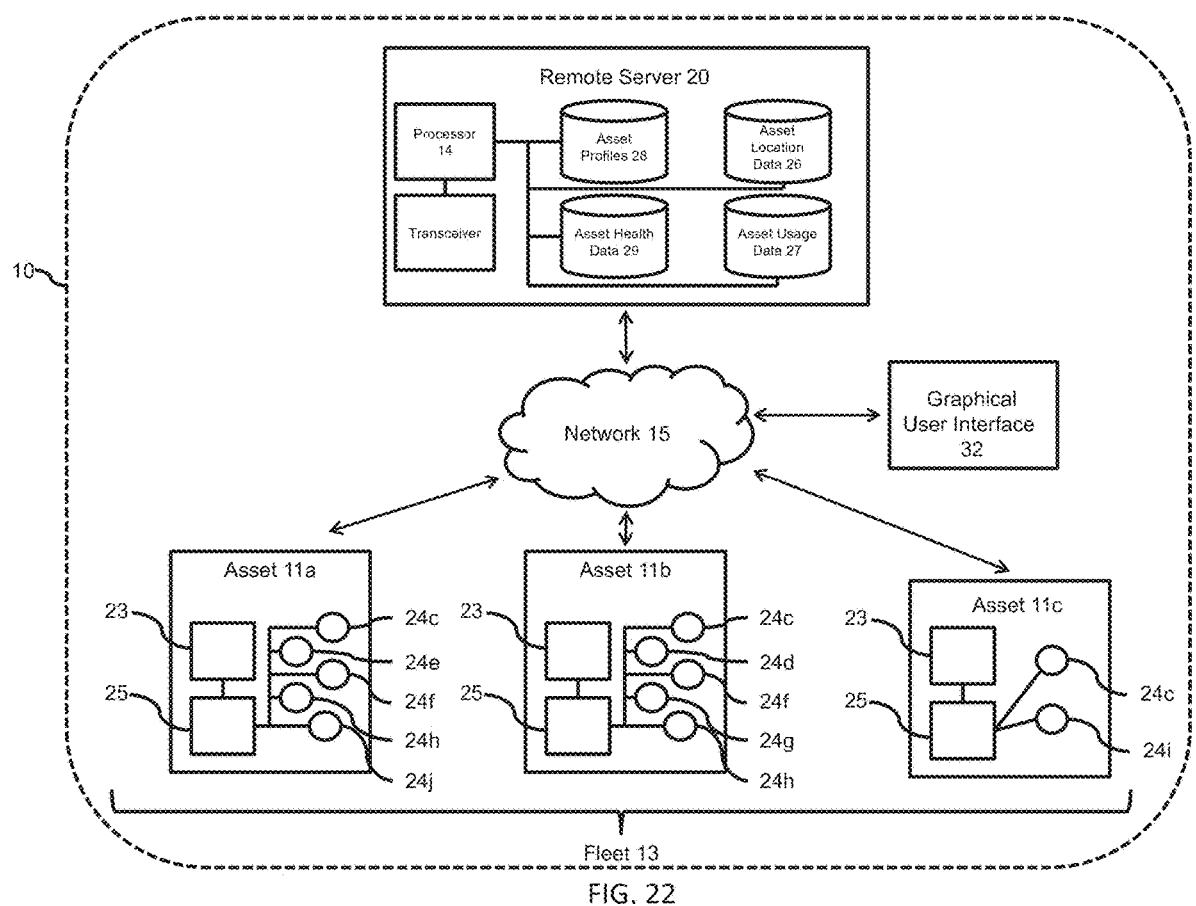
FIG. 22 is a third exemplary embodiment of an asset management system having assets with varying sensor arrays resident on assets.

In another embodiment as shown in FIG. 22, an asset 11a may be equipped with a power consumption meter 24c, a 6-axis gyroscope 24e, a magnetometer 24f, a vibration sensor 24h, and an NFC reader 24j, wherein each sensor 24 is operable to determine when conditions occur involving certain uses of the asset and to communicate those events to the AMS 10. A second asset 11b may be equipped with a power consumption meter 24c, an accelerometer 24d, a magnetometer 24f, a key stroke monitor 24g, and a vibration sensor 24h, wherein each sensor 24 is operable to determine when conditions occur involving certain uses of the asset and to communicate those events to the AMS 10. A third asset 11a may be equipped with a power consumption meter 24c and a proximity sensor 24i, wherein each sensor 24 is operable to determine when conditions occur involving certain uses of the asset and to communicate those events to the AMS 10.

In one embodiment, direct use states can be measured indirectly, so as not to incidentally capture Patient Information Act or Health Insurance Portability and Accountability Act controlled data. Direct use can be measured via power use measurements. These measurements are dynamic, seeking whether a particular device is in a non-use norm, or whether the device exceeds the threshold power usage used to determine active use of the device. In this manner, an addition of accessories does not require a manual recalibration of baseline power use. A power use sensor 24a is operably coupled to the asset 11 so as to determine the power use of the asset 11 without actually capturing the data or information being used by the asset 11. For example, power usage may be monitored on a mobile workstation by monitoring how much power is being consumed by the workstation when a clinician is directly interacting with the workstation versus when the workstation is standing idle. Because the AMS 10 is dynamically updating the power usage, when additions of accessories to an asset 11 occurs, the AMS 10 is able to determine the use state of an asset 11 even when the power consumption and power requirements have been altered by the addition of the accessories.

In some embodiments, the back current draw is used to determine the use state of an asset 11. The AMS 10 may be operable to detect varying bands of current draw from an asset 11 or a plurality of assets. In one example, when a station is in an off-state, minimal power will be drawn from a power source. Thus, if the power drawn from the power source is within a predetermined range or band of power characteristic of a device in on off-state, the asset 11 may be assigned a "not in use" designation for that time interval. Different tasks on different devices have varying power demands. Therefore, an asset 11 can be characterized based on the power demands and the type of asset requiring the demands. A sensor 24 is operably coupled to the asset 11 and specifically the power interface between the electronic components and the power source such that the sensor 24 is capable of detecting the back current draw. The sensor 24 is operable to send a signal to a processor 14. In some embodiments the signal contains data packets regarding the power use or back current draw of the asset 11. The processor 14 is then able to interpret the signal and able to determine by a proprietary algorithm the use state of the asset 11. A memory storage device is operable to store the signal or data packets from the sensor as well as the interpreted data and signal from the processor 14.

Furthermore, the AMS 10 may determine if multiple assets 11 are being utilized on a station. The AMS 10 is able to determine the power demands on specific ports of a workstation. In one example, a printer may be connected to the AMS 10 via a USB port on the workstation. The AMS 10 is able to detect the power demands from the USB port and determine the use of an accessory, auxiliary, or peripheral device on the workstation. The use of accessory, auxiliary, or peripheral devices may also be classified based on bands or ranges of power demands. Power demands may be measured by current or voltage demands, or any other method known to one of skill in the art.

As the power demands of a workstation and the accessory, auxiliary, or peripheral devices associated therewith are recorded and stored, the AMS 10 is able to assign use states to the workstations and devices. The use states and patterns may be associated with a profile 28 of each asset 11 stored on a memory storage device. The use and patterns of use may further be implemented to manage and allocate resources within a fleet. Based on the information, the AMS 10 may make recommendations to more efficiently allocate resources. In one example, if an Emergency Department has ten (10) workstations, all of which have been assigned the status of HIGH ROI based on direct use during peak usage periods, whereas the Intensive Care Unit has twenty (20) workstations, but only ten (10) of the workstations are assigned the status of HIGH ROI during peak usage periods, the AMS 10 may recommend that five (5) of the Intensive Care Unit's mobile workstations be reallocated to the Emergency Department. The AMS 10 may also recommend the procurement of more devices if all devices in a department or fleet have been assigned the status of HIGH ROI in order to prevent downtime due to device failure or maintenance.

Figure 9:
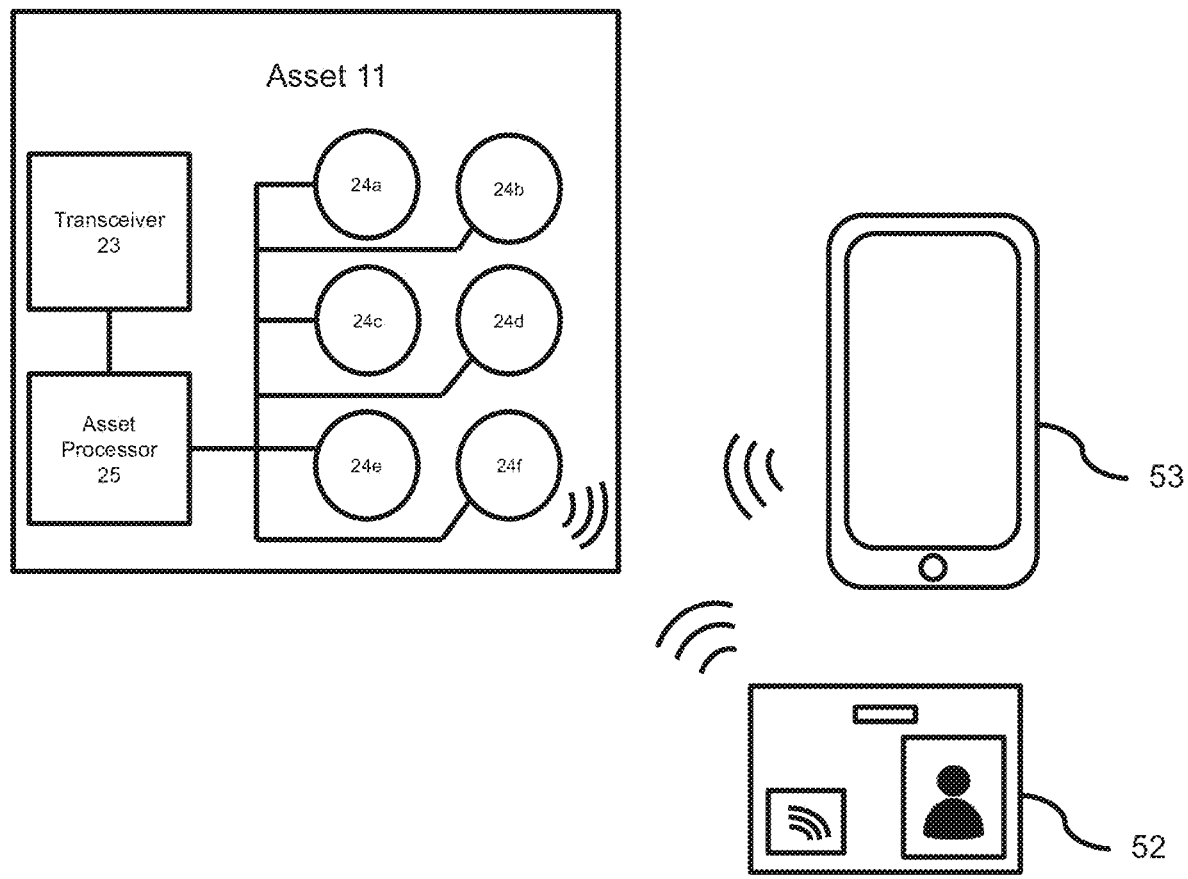
FIG. 9 is an exemplary embodiment of an asset authenticating a user and setting a use state for a device based on proximity of a user.

Returning to use states, direct use states or use states can be measured using asset location and proximity data. In one example, "At the Ready" is measured via location of the device and proximity of a given clinician to the asset. Location of an asset 11 and the proximity of a clinician to the asset 11 may be determined with location devices 12 deployed on the asset and the clinician. In one example, a mobile workstation may include an RFID or NFC reader 24f which is operable to detect an NFC tag or RFID chip which has been placed in a clinician's identification badge 52 or by NFC and RFID in a mobile phone 53, as shown in FIG. 9. When the clinician is within the operable proximity of the mobile workstation's RFID or NFC reader, the RFID or NFC reader authenticates the clinician via a network 15, update a server 20 of the proximity of the clinician to the mobile workstation. When this occurs, the AMS 10 is able to update the use state of the mobile workstation to "At the Ready." In another example, the RTLS 30 portion of the AMS 10 as described previously may be deployed to locate a mobile workstation within a facility, wherein the location data 26 is stored, dynamically updated, and associated with an asset profile 28 in the AMS 10. A similar method of tracking clinicians may also be implemented. When this occurs, the AMS 10 may monitor the location of a clinician relative to the mobile workstation. When the AMS 10 determines that the clinician is within a threshold proximity of the mobile workstation, the AMS 10 updates the asset profile 28 for the mobile workstation to "At the Ready" based on the relative location of the clinician to the mobile workstation.

As another example, "In-Transit" is directly measured via accelerometers, distance counters and other such transducers and devices. In other embodiments, "In-Transit" may be determined based on location data 26 associated with the mobile workstation from one moment to the next. If the AMS 10 determines that the location data 34 associated with the asset profile 28 demonstrates that the mobile workstation has moved to a second location during a period of time, the AMS 10 may update the use state of an asset 11.

"In-Use" is determined on a periodic basis, and each device is identified as either being in use or not in use for that measured period. A variety of different types of use states may be readily apparent to one of skill in the art. The system is operable to determine which use states will be profiled as "In-Use" and "Not-in-Use."

In some embodiments, the day is divided into increments of time (including but not limited to hours or minutes or seconds). Any asset 11 in use for one or more measures during that increment is assigned a direct use state of "In Use" for that increment. Any asset 11 that records any use state other than "Not-in-Use" during an increment is assigned an "In-Use" state. In other embodiments, an asset 11 is assigned the state in which the asset 11 was for the majority of the interval. In one example, when the interval is selected at one hour increments, when an asset 11 is "Directly-in-Use" for 28 minutes, "In-Transit" for 5 minutes, and "Not-in-Use" for 27 minutes, the asset 11 will be assigned a state of "directly in use" for the hour interval. In other embodiments, the asset 11 will be assigned a state of "In-Use" for the hour interval. The two examples vary in the assignment of state under the same set of facts as the first example is more specific to the state the asset 11 was assigned based specifically on the state of the device during the hour interval, whereas the second example demonstrates the assignment of a state based on the combined totals of specific categories, which together form a broader category of use. Thus, in the second example, the assignment of "Directly-in-Use" and "In-Transit" are combined into a single category defined as "In-Use."

Figure 10:
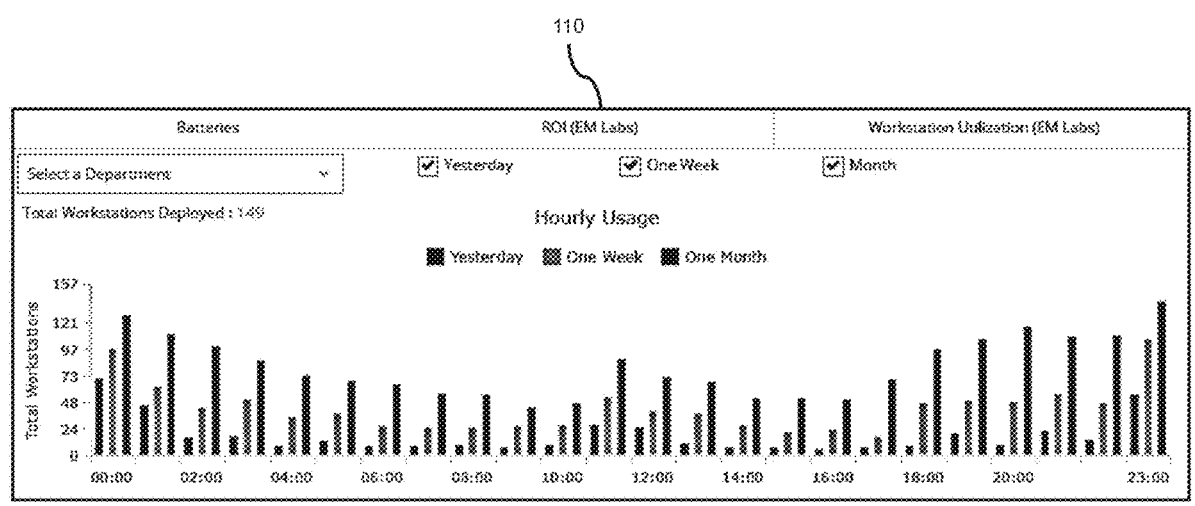
FIG. 10 is an exemplary embodiment of a column bar chart usage of a fleet of assets broken down into hourly usage.

In one embodiment, data for each asset 11 is placed in a usage table 110 and is assigned a state of "In-Use" or "Not-In-Use" for each asset 11 and each increment or period of time, as seen in FIG. 10. For each period, the number of devices (either in total or grouped by work area and/or type of equipment) is counted and compared to the available assets within the same grouping. This data may be displayed in tables and/or charts. Workstation Fleet ROI may be displayed in a heat map format, as in FIG. 11, or a column bar format 112, as in FIG. 12.

In some embodiments, a subset of increments are flagged as high-use periods. Maximum usage may be identified in order to assess whether a facility has an appropriate number of assets 11, in total or by group, and for ROI determinations.

In other embodiments, ROI data may be integrated into battery health data (or asset condition data) 29 and can be used to develop predictive models of battery lifespan. In one example, the use states of an asset 11, for example a battery, may be used in the algorithm for determining the predicted functional lifespan of the battery. If a battery is constantly in an "In-Use" state, the predicted lifespan of the battery may be shortened. Thus the use state data 27 that is associated with the profile 28 of an asset 11 may be used as an additional factor in the determination of asset health or predicted asset health.

Device ROI can be determined over any period (such as daily, 7-day, 14-day or any other suitable measurement period). Within those parameters, any device that is in use in any of the "High Use Periods" is flagged as "High ROI". Thus, ROI is the percentage of how many "High Use Periods" in which a given device (or group of devices) is used as a ratio of the total number of "High Use Periods" in the measured timeframe. In one example, a subgroup of a fleet 13 of mobile workstations may be deployed in a surgical unit of a hospital. The subgroup of the fleet of mobile workstations may include 10 mobile workstations. Over the course of a week period the system monitors the use state data 27 associated with each of the mobile workstations and determines when the most mobile workstations are determined to be "In-Use." For those periods when the most mobile workstations are "In-Use" the system designates those periods as "High Use Periods." The AMS 10 then analyzes the use state data 27 associated with each of the mobile workstations during the high use periods. A first mobile workstation may have been assigned an "In-Use" state during 7 of the past 10 "High Use Periods." The mobile workstations may be assigned a 70% ROI based on the number of times the mobile workstations was "In-Use" during the "High Use Periods."

In one embodiment the ROI data may be based on flagged high use assets. This allows the AMS 10 or a user to allocate assets 11 throughout a facility more efficiently based on the ROI data. In one example, if an asset 11 is being used only intermittently in one department whereas another department has a lack of assets, the asset 11 may be reassigned to the department with insufficient assets. Likewise, the AMS 10 may record use patterns and determine certain types of assets that may be better suited to the type of use of another department. In one example, a battery with a high charge capacity may not be efficiently used in a department which uses the battery for short periods, where a battery may be charged in the intervals between the short periods of use. The battery with a higher charge capacity may be allocated to another department or for types of use that requires use over long periods of time without recharging. Another example might be a battery with the voltage and current capacity to power several devices is allocated to a station that powers several devices whereas a lighter battery may be allocated to a mobile station.

In some embodiments, the ROI data for an asset 11 may be used to modulate or allocate assets within the fleet based on indirect data or direct use state. Certain assets 11, either individually or in groups, are not available to be reallocated, and are defaulted to "High ROI" for each measured period. In a given embodiment, these assets 11 will have a 100% ROI for the measured period so as to not indicate available assets 11 when they are, in fact, not available for use elsewhere in a facility. ROI may be determined and put into a table where it can be displayed via reports or various displays, including those previously described.

In a further embodiment, the AMS 10 is able to make recommendations based on the use of accessory, auxiliary, or peripheral devices. Because the AMS 10 may track the use of accessory, auxiliary, or peripheral devices, the AMS 10 may determine when an accessory, auxiliary, or peripheral device is being underutilized and may be more efficiently utilized on a different workstation. For example, a workstation may be connected to a printer. If the printer is being underutilized according to a predetermined threshold or comparative data from other workstations, the system may recommend reallocating the printer to a different workstation or a different department.

In other embodiments, the AMS 10 may use current draw data to flag assets in need of maintenance. In some instances, an asset 11 may be improperly functioning, and based on the type of current draws from a station, the system may be able to detect that the asset is improperly functioning. For example, a mobile workstation may have abnormal power consumption. The AMS 10 may detect this abnormal power consumption and flag the mobile workstation. In other embodiments, a clinician may know that a mobile workstation is improperly functioning but has not made a report regarding the defect in the mobile workstation. The AMS 10 is able to detect abnormal patterns of use based on a proprietary algorithm which triggers the AMS 10 to set a maintenance flag on the mobile workstations profile 28.

In some embodiments, patterns are recognized over long periods of time. Thus periods of high use for an asset in a department may not only be limited to certain times of the day or days of the week. In one example, the AMS 10 may be able to track use data over several years and recognize patterns of high demand in certain departments, such as higher use in Labor and Delivery during summer months, higher use in the Emergency Department around holidays and football season, higher use in Family Medicine Department during flu season, etc. Thus, the AMS 10 is able to reallocate resources during certain busy seasons based on previous trends determined by the data recorded, stored, and analyzed by the AMS 10.

In some embodiment, the patterns of use of individual assets and groups of assets 11 establish a baseline or normal use pattern. When an asset 11 falls outside that use pattern, the AMS 10 can flag the device. An asset 11 may be flagged due to a failure or another situation that results in the asset 11 being unavailable for use. A normal use pattern may be an aggregation of data recorded on the asset 11. In other embodiments, it may be a manufacturer recommended use. Analytics within the AMS 10 may be run to optimize the use of the devices and assets 11 to allocate them in the most efficient manner. When an asset 11 falls outside a threshold of "normal use", an alert may be created.

In another embodiment, once an asset 11 is flagged as a problem, the AMS 10 may perform one or more functions based on the flag. The AMS 10 may send notifications by various means such as email, on-screen notices, and other alerts to individuals responsible for maintaining and repairing the devices. The AMS 10 may trigger or activate a screen or an optical/audible indicator of the flagged device as an alert, including messages such as "Check Cart", "Check Battery", or other check indicators. Such indicator can be an illumination or an icon.

In another embodiment, the AMS 10 may read fleet and network-level patterns to enable metric tracking. For example, a "Normal Pattern" can be established over time, using the data received and stored regarding the usage level of the asset 11 or group of assets. When the usage is periodic, a shorter time period is required to establish a reliable baseline of use.

In some embodiments, an ROI determination may be continually performed for each workstation and battery. The ROI determination may be based on the use during a given period, compared to a target usage as represented by a fully used asset 11 during peak periods of a day. Certain assets 11 can be designated as or assigned a "HIGH ROI" status based on their intended use in a facility (e.g. Emergency Room, OR, etc.). Each day can be measured hour-by-hour to determine if a given asset is in use during that hour or not. Peak usage hours can be established for each department based on the maximum assets 11 in use for each hour of the day.

In some embodiments, if a workstation is in use during peak usage hours, the workstation is flagged as HIGH ROI. Batteries are flagged as HIGH ROI if the batteries are used during peak usage hours, or used in a workstation anytime within the next 24 hours. Over multiple increments, each asset is given a rolling average ROI based on how many days the asset is flagged as HIGH ROI as opposed to days not flagged as HIGH ROI. In one embodiment, assets are color-coded into a chart or graph showing the ROI over user-selectable time frames (for example: a day, week, 14 days, etc.).

In one embodiment, the AMS 10 is provided for managing, monitoring, and allocating assets 11 in a facility, including a plurality of assets 11, a plurality of sensors 24, each sensor 24 of the plurality of sensors 24 coupled to an asset 11 of the plurality of assets, the plurality of sensors 24 operable to sense an asset condition and generate a signal when the asset condition is met, a processor 14 operable to receive the signal and generate a heat map 16, wherein the heat map 16 is arranged such that a plurality of signals are assigned a color to represent the asset condition and each color is grouped with a group of like colors, and a display operable to receive the heat map 16 and display the heat map 16. In some embodiments the AMS 10 may be configured to determine ROI.

In one embodiment, the ROI data can be used to determine the probability of a workstation having already failed (become unusable) or approaching failure, allowing for preemptive ordering of stations or maintenance.

In another embodiment, a method of managing a plurality of assets 11 and determining a ROI of the plurality of assets 11 comprises sensing use of plurality of assets 11 during a period of time, determining high use periods for the plurality of assets 11, and flagging high use assets of the plurality of assets 11 having a threshold use during the high use periods.

In one embodiment, current failure is determined by comparing the rolling use average of a workstation, during the busiest hour or hours of the day against the current use of the workstation. A gate test can then be used to evaluate an average workstation use (across a department or fleet) during the peak use hour or hours, and compare the average workstation use to each workstation's current use to see if current use falls below a predetermined percentage of the workstation's average use. A workstation that fails this test is flagged as "likely broken" and notifications are sent and a status is set to indicate the likely condition.

In some embodiments, the workstation use-percentage is determined for peak use hour or hours and a running average is retained. If the current use falls below a dynamic band around the running average, a workstation is flagged. The AMS 10 provides a prediction of when the workstation will no longer be usable based on the data and trend recorded by the AMS 10. In some embodiments, the AMS 10 uses a proprietary algorithm to predict the failure date. That predicted date may be mapped to a color heat map 16.

In some embodiments, the predicted current failure and predicted future failure (a time frame configurable by a user or manufacturer) is indicated on the user interface or workstation screen (touch screen, PC screen, etc.), via a "check workstation" icon as depicted in FIG. 4. Additionally, certain measurements (including, but not limited to, voltage, current, temperature, accelerations, impacts, loads, and other factors) will trigger the check workstation indication and send a notification to the customer and service department of the manufacturer. Use-hours, distance, or a combination of use-hours and distance can trigger the check workstation indicator. Indicators can be used on screen, in email and other messages, and in reports to indicate workstations that are in need of service.

In another embodiment, when an asset has been flagged or is otherwise in need of technical assistance, repairs, or attention from IT, the system allows for a computer on a mobile workstation to be remotely rebooted. Thus an IT tech does not need to be deployed directly to the mobile workstation to perform a reboot of the system. The system is also operable to perform remote troubleshooting of assets 11.

Graphical User Interface

A next aspect of the disclosure includes a graphical user interface 32 for providing a user with a dynamic snapshot of assets 11 and a fleet 13 of assets including health, charge, location, ROI of assets 11, and recommendations based on real-time data for allocating resources and maintaining an effective and efficient fleet 13. The disclosure further provides for a graphical user interface 32 capable of providing dynamic analysis of a fleet of assets 11 in the context of computerized asset management. Various embodiments of the graphical user interface 32 have previously been described.

Figure 13:
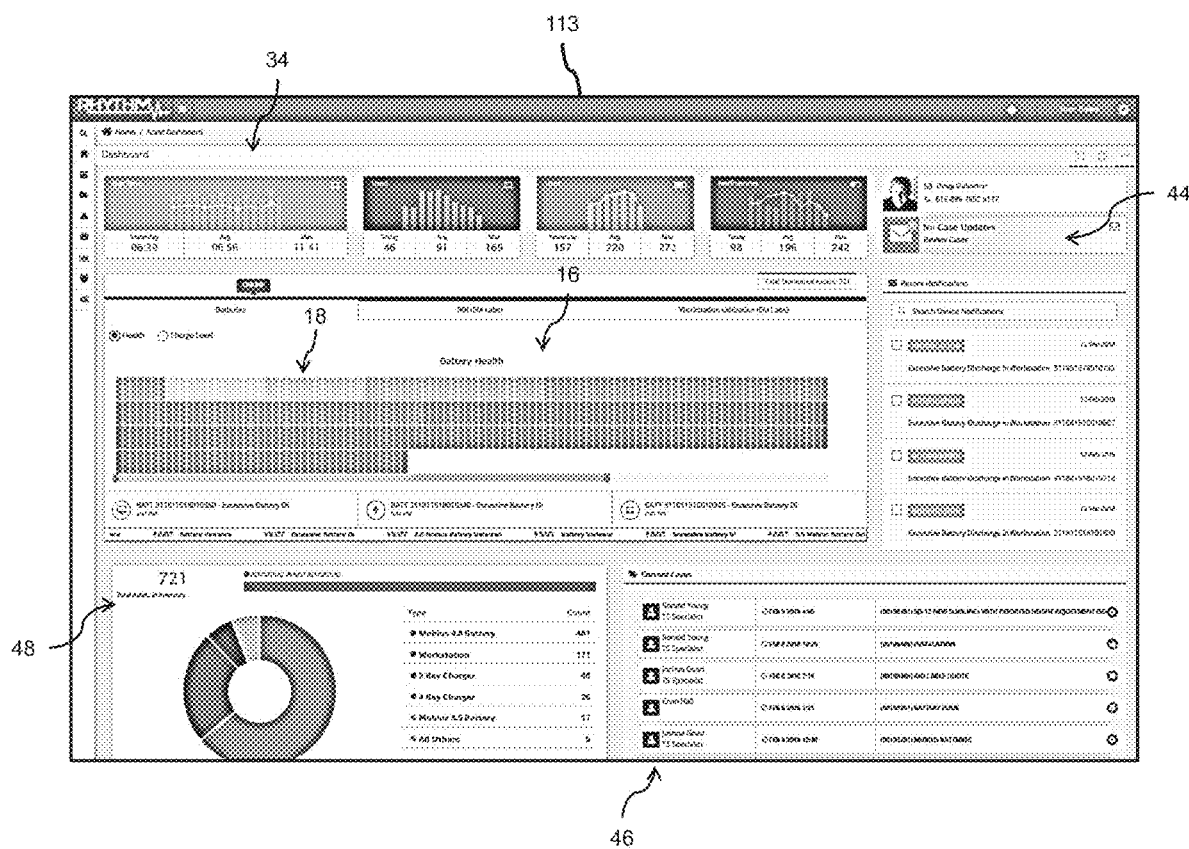
FIG. 13 is an exemplary embodiment of a homepage of a graphical user interface.

In one embodiment the graphical user interface 32 provides a home screen 113 in which a variety of information may be displayed and is a launching point for all of the activities within the AMS 10, as seen in FIG. 13. The graphical user interface 32 may provide a main menu, dashboard views and graphs 34, case status 44 and contact information including communication channels, recent notifications, assets in inventory summary 48, and current case information 46. The information displayed in each feature and module of the graphical user interface 32 may be dynamically updated to provide a user with real time analysis of the status, health, and usage of a fleet of assets. The home screen may include a display of battery information, including battery health and battery charge level. As discussed above, battery health and battery charge level may be displayed in a heat map 16. The AMS 10 can dynamically update the heat map 16 based on the data associated with each specific battery's profile 28. For example, as the AMS 10 receives charge data on a battery that is actively being discharged, the charge level of the battery might drop below a second charge level of a second battery. The AMS 10 dynamically updates the position of the representation 18 of the battery relative to the position of the second representation of the second battery. Furthermore, the AMS 10 is operable to dynamically update the representation 18 as the battery charge level or health drops below a specific threshold. For example, when a battery charge level drops below 35%, the graphical user interface 32 is updated such that the representation of the battery is provided as a red rectangle. See FIG. 2 and FIG. 6.

The home screen of the graphical user interface 32 may also be operable to provide a graphical representation of the assets 11 in inventory for a fleet of assets. The representation may specifically divide the assets up by the types of assets, such as workstations and batteries, as well as by make and model.

Figure 14:
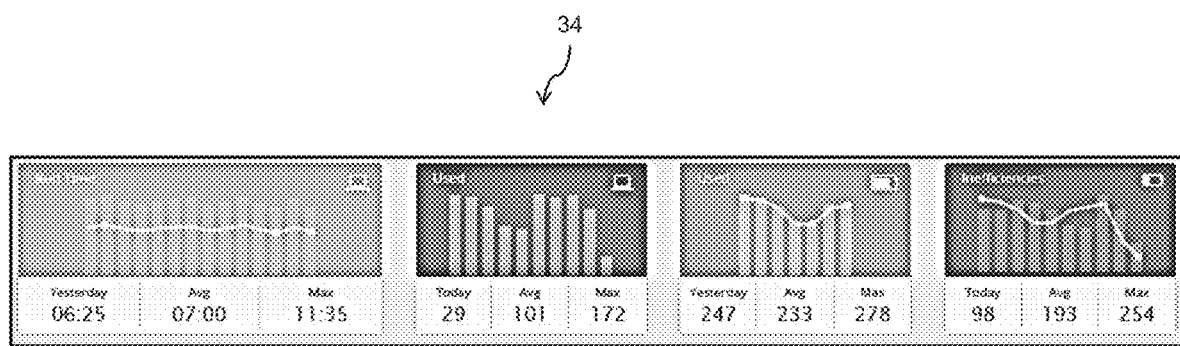
FIG. 14 is an exemplary embodiment of a dashboard view on a graphical user interface.

Referring to FIG. 13 and FIG. 14, dashboard views 34 may be provided on the graphical user interface 32 which includes dynamically updated information and snapshots of the fleet 13 and assets 11 of the fleet including run time of the assets, mobile workstation usage, batteries used in that day, battery inefficiencies, and more detailed information displayed on each of these views when by hovering the cursor over a portion of the dashboard views, an example of the hovering can be seen in FIG. 6. This provides a fleet 13 overview including the status and use of the assets 11 in the fleet, providing a dynamic picture of the use and health of the fleet 13 and assets 11.

Each representation of a battery may be embedded with additional information that can be accessed via a link or an action. For example, a user may hover a cursor over a specific battery and the graphical user interface can display the battery identification number, the charge level, or any other data that might be relevant, as seen in FIG. 6. If a user selects the representation, the AMS 10 is operable to display more detailed information or all of the information associated with the battery and battery profile, as seen in FIG. 4.

Figure 11:
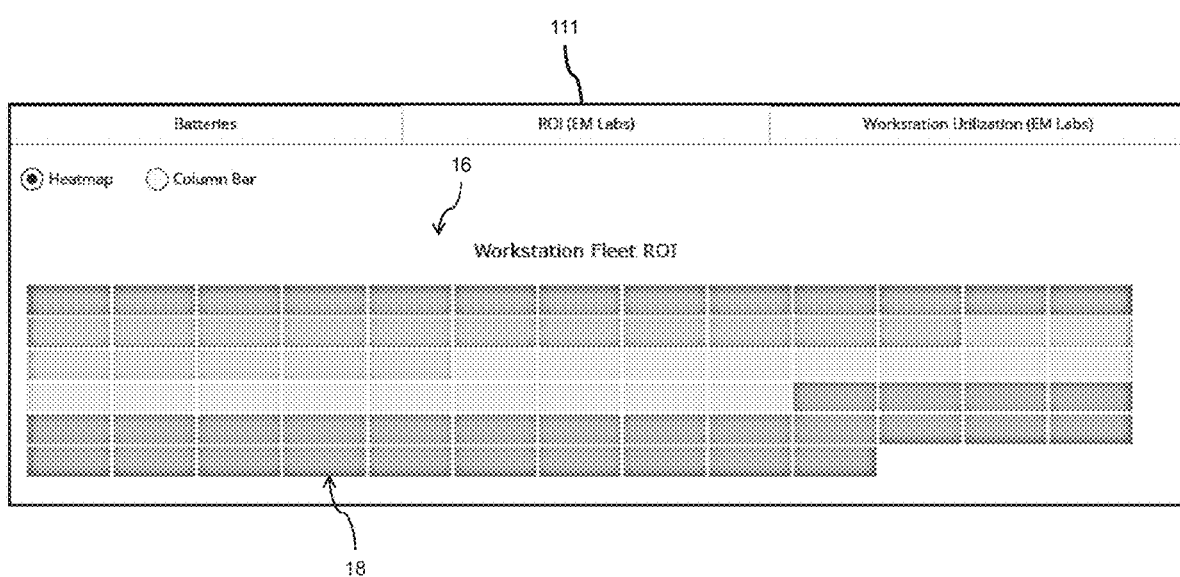
FIG. 11 is an exemplary embodiment of a heat map of the return on investment of a fleet of workstations.
Figure 12:
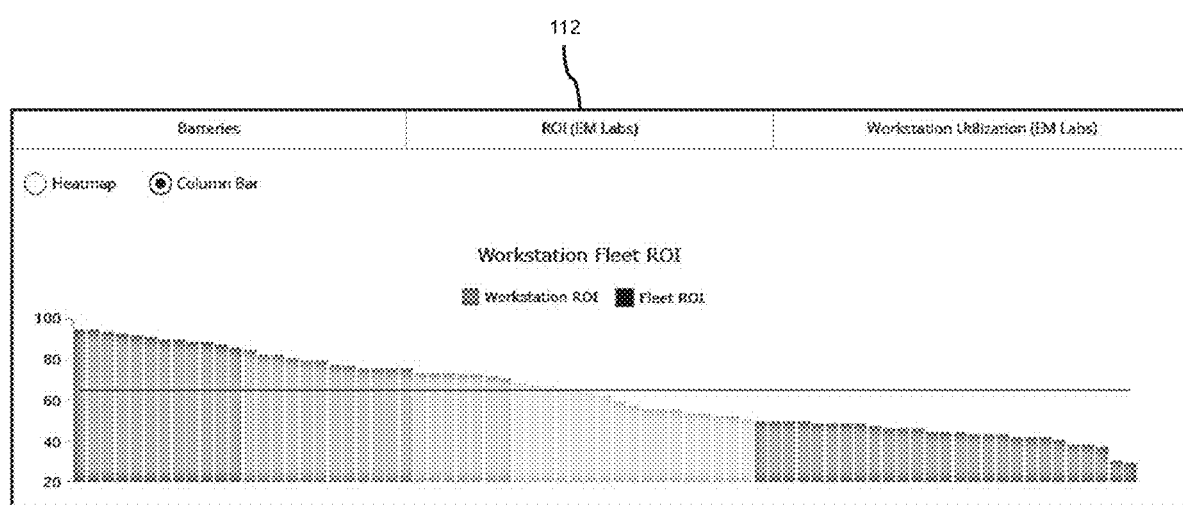
FIG. 12 is an exemplary embodiment of a column bar chart of the return on investment of a fleet of workstations.

The graphical user interface 32 may also be operable to display information regarding the ROI of a fleet of assets, as seen in FIG. 11. The AMS 10 dynamically provides this information to the display to provide a real-time snapshot of the use and allocation of assets 11 within a fleet 13 of assets. As previously discussed, the AMS 10 is operable to determine a ROI for specific assets 11 within a fleet 13 of assets. The graphical user interface is able to provide that information in a heat map format or a column bar format. As the ROI of certain assets 11 change overtime, the position of the graphical representations 18 used to denote a specific asset 11 may be moved relative to another asset and the symbol 18 may be altered to represent a change, such as the symbol changing from a yellow color to an orange color when an asset drops below a threshold ROI. As discussed with regards to the batteries, the graphical user interface is operable to provide supplemental information when certain actions are taken. A user is able to determine which assets 11 may be underutilized and reallocate the asset 11 for another purpose or to another department based on the ROI data. In other embodiments, the AMS 10 is able to determine which assets 11 may be underutilized and where the assets 11 may be more efficiently and effectively used, such as in a department that has 100% ROI assigned to each asset 11 assigned to that department.

Figure 15:
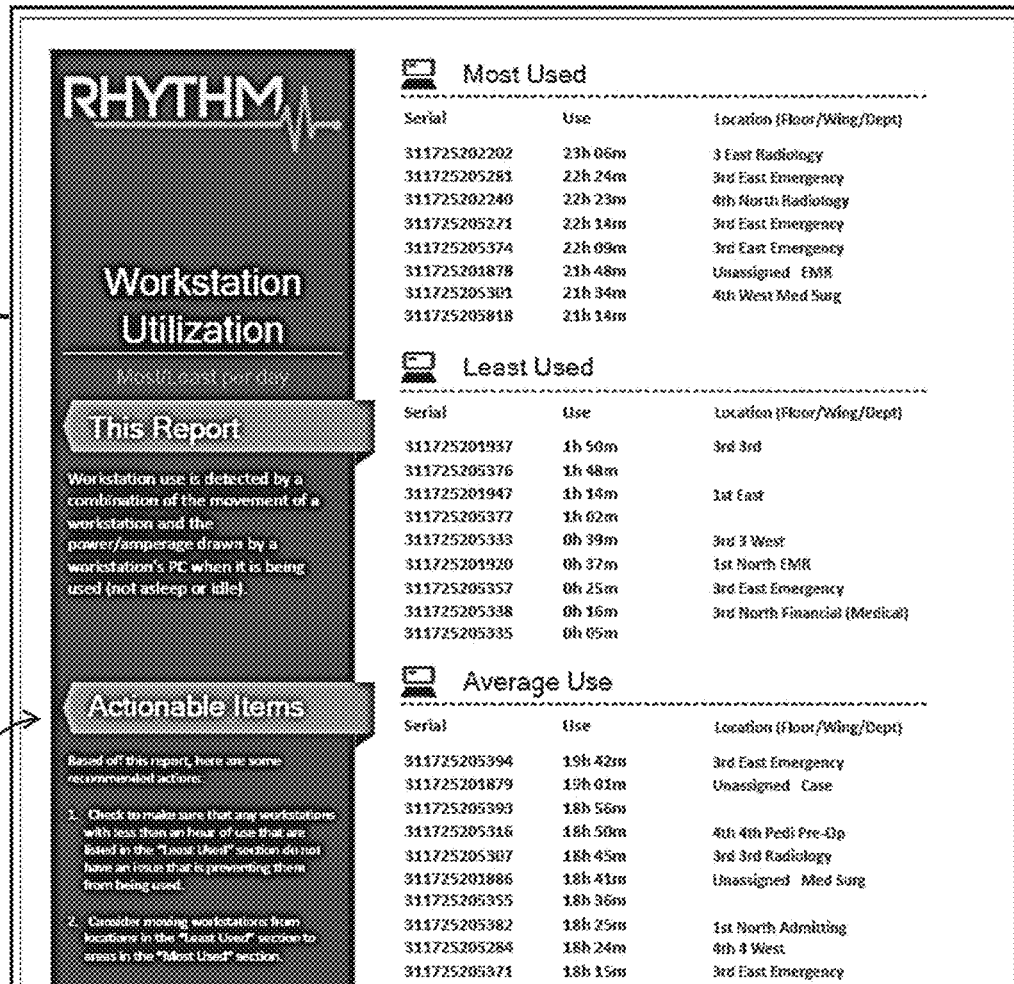
FIG. 15 is an exemplary embodiment of a workstation utilization view on a graphical user interface.

The graphical user interface may also be operable to provide graphical representations of workstation utilization, as seen in FIG. 10. Workstation utilization demonstrates how many assets 11 in a fleet of assets 13 are being utilized during specific time intervals. For example, the workstation utilization interface can display the number of workstations that are being used between 1:00 pm and 2:00 pm, including the numbers of workstations that have been used in the past day, the past week, and the past month. The user can refine the display by selecting specific departments for which this data may be displayed. This allows a user to ascertain what periods of time the most utilization and need of workstations might be during certain times of the day, including which departments. A user then may allocated various assets 11 across the departments at different time periods based on this information. In another embodiment, the AMS 10 may make recommendations on the allocation of assets 11 across different departments based on the workstation utilization, as shown in the workstation utilization report 115, one embodiment being depicted in FIG. 15.

The graphical user interface 32 may also be operable to provide a graphical representation of the open work orders relating to the fleet of assets. Each work order may be managed within the AMS 10 and can be accessed from the home page. The AMS 10 is operable to integrate into existing IT systems and workflow, allowing existing ticketing systems to be maintained. Information regarding case orders may be presented directly on this page and more specific information may be accessed within the work order component, which can be directly accessed by selecting the desired work order on the graphical user interface.

The graphical user interface 32 may also be operable to display graphical representations of recent notification regarding the AMS 10 and assets 11. It also provides an interface for communicating directly with representatives for servicing the AMS 10.

The graphical user interface 32 may also be operable to display graphical representations of run time for workstations, use of workstations and batteries and inefficiencies of workstations and batteries. Each of these representations may be selected to provide specific details regarding the assets for which the representations are presented, including recommendations for reallocation, replacement, or supplementing assets 11 within the fleet 13 of assets. Further discussion of how these determinations have previously been discussed in preceding sections, including battery health and ROI.

The graphical user interface may also be operable to display specific interfaces for viewing only battery information, only workstation information, and only charging station information, examples of which can be seen in FIG. 4 and FIG. 5. Within each of these interfaces, information may be sorted based on various factors including charge level, health, usage, cycle count, reporting wing and department, location, and other factors known to one of skill in the art. Furthermore, the AMS 10 provides an option to locate 36 the nearest battery, workstation, or charger based on the location data by selecting an option on the graphical user interface. The AMS 10 is able to locate, based on the relative locations of the unit in use and the desired unit, where the closest desired asset 11 is located. The AMS 10 may provide a specific location, and may also send a signal to the desired asset which triggers an audible or visible notification to be transmitted by the desired asset 11.

An updates display may be provided on the graphical user interface which includes real-time updates and dynamically monitored status and recommendations to a user. In one embodiment, this includes critical updates such as recommendations to replace assets or parts, servicing assets, added or removed assets 11 to the fleet, software updates on the assets 11, and any other notifications known to one of skill in the art.

The AMS 10 is operable to provide a dashboard status report, which is operable to display to a user via the graphical user interface a daily snapshot of the metrics of the system. The dashboard status report includes runtime of the batteries in the fleet 13, units used including the mobile workstations logging activity, batteries used including the count of batteries logging a complete cycle, inefficiencies including logging events in which a battery was not fully utilized, peak including the time of day that shows the most activity from the mobile workstations, dip including the time of day that shows the least activity from the mobile workstations, the average uptime of mobile workstations from the previous day, daily average of uptime average of mobile workstations, top five (5) hours of the day including the total number of mobile workstations active during an hour and the total number of workstations in the fleet, assets in inventory including a breakdown of types of assets, and charge levels and health of batteries in the fleet 13.

The AMS 10 is operable to provide via the graphical user interface a user with a six (6) month battery prediction based on the batteries specific operating condition and capacity of health, an example of which is shown in FIG. 7. The battery planning calendar assists users with planning for potential battery replacements in the fleet. This includes a projection of batteries that will fall below a health level threshold during a given month. Included in the projection via the graphical user interface 32 for consumption by the user are the serial numbers of those batteries that will fall below a specific health level threshold. The serial number also provides a link to the battery so the battery information may be accessed via the graphical user interface which allows a user to access related information such as warranty information and dates associated with the specific battery as well as location data, including the ability to send a command to the battery via a wireless network 15 to emit a visual or auditory notification for locating the battery.

Figure 16:
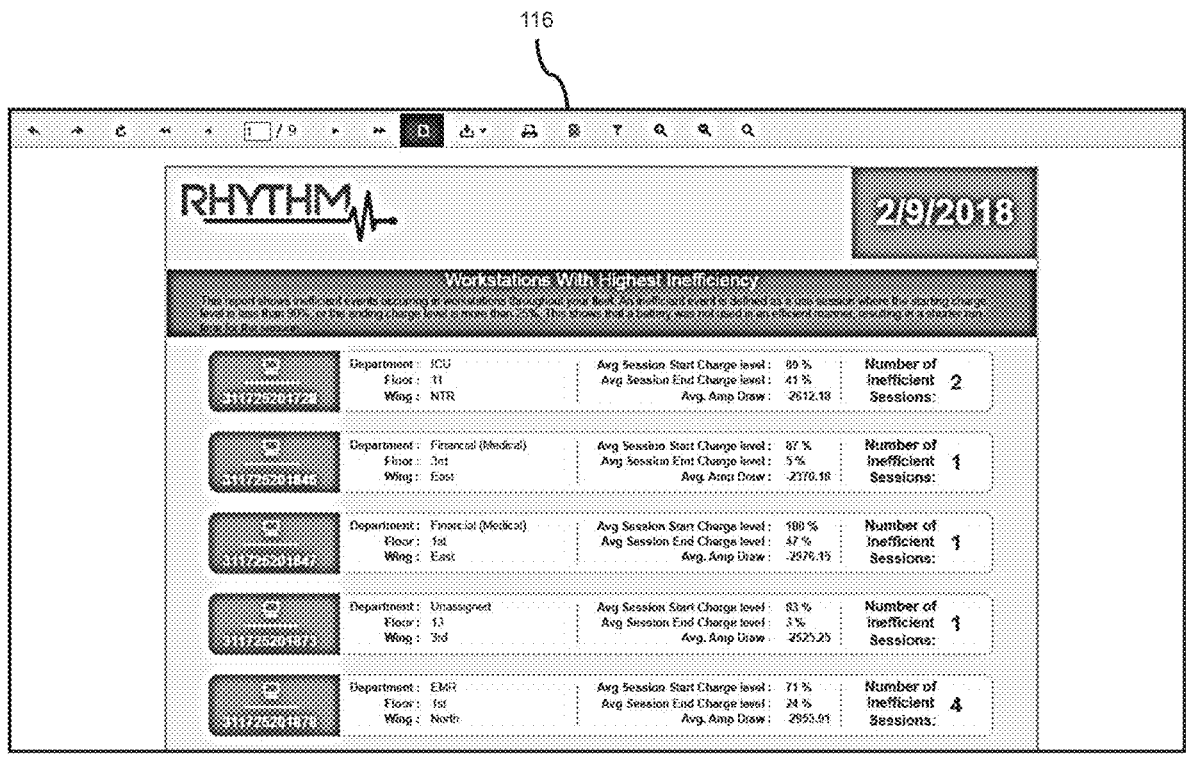
FIG. 16 is an exemplary embodiment of a inefficiency chart view on a graphical user interface.

Included in the graphical user interface is a workstation inefficiency report 116 which may be generated by the AMS 10 for consumption by the user, an example of which is shown in FIG. 16. The workstation inefficiency report is operable to display inefficient events occurring in workstations throughout a fleet 13 of assets. The AMS 10 analyzes and compiles the data provided by the mobile workstations to the server 20 to provide a dynamically updated snapshot of the workstations with the highest inefficiencies, including the number of inefficient sessions, the department, floor, and wing in which the inefficient session occurred, and the average session start and end charge level. The inefficiencies may also be partitioned based on departments.

Other elements of the graphical user interface include warranty information, alerts, notifications, cases, dashboard results, users, and settings.

Figure 17:
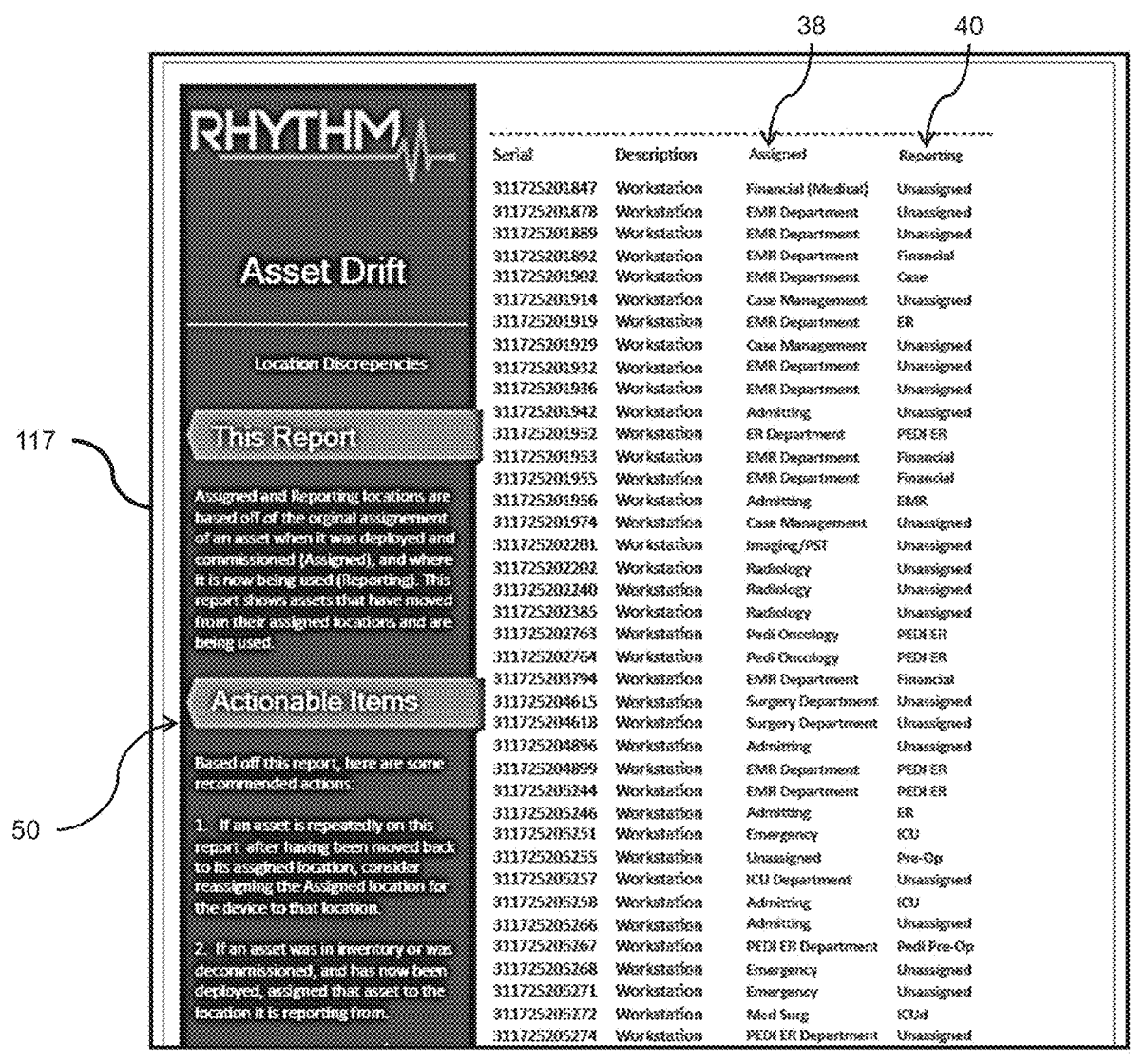

The graphical user interface is also operable to display assets 11 which have drifted from the location to which the assets 11 are assigned in the asset drift report 117, an example of which is shown in FIG. 17. The asset drift report identifies which workstations have a reporting location 40 different from the workstation's assigned location 38. Included in the report art actionable items 50 which are a list of recommended actions that may help produce a more efficiently allocated fleet 13 of assets 11. For example, the Asset Drift Report may include recommendations such as, "If an asset is repeatedly on this report after having been moved back to its assigned location, consider reassigning the Assigned location for the device to that location."

The graphical user interface 32 provides a user access to dynamically updated information, calculations, predictions, and suggestions of a fleet 13 of assets 11 that is powered by the AMS 10. The graphical user interface provides up-to-date and predictive snapshots of a variety of problems identified in the prior art pertaining to fleet and asset management and allocation for an efficient and effective fleet.

Thus, although there have been described particular embodiments of the present invention of a new and useful BATTERY AND WORKSTATION MONITORING SYSTEM AND DISPLAY, it is not intended that such references be construed as limitations upon the scope of this invention.

What is claimed is:

1. A mobile workstation comprising:
   a cart movable between locations in a facility;
   a transceiver configured to wirelessly send to and wirelessly receive data from, via a wireless network, at least one remote server;
   a first sensor configured to generate asset location data, wherein the asset location data includes an actual location and an assigned location for the mobile workstation; and
   a second sensor configured to generate use state data when a specified event occurs relating to the mobile workstation,
   wherein the transceiver wirelessly sends the asset location data and the use state data to the at least one remote server, and
   wherein the at least one remote server performs the steps of:
      determining, based on the use state data, a use state of the mobile workstation;
      providing, via a user interface, an option to locate the mobile workstation;
      comparing, based on the asset location data, the actual location of the mobile workstation to the assigned location of the mobile workstation; and
      providing, via the user interface, a first notification indicating that the actual location of the mobile workstation corresponds to the assigned location of the mobile workstation.

2. The mobile workstation of claim 1, wherein the at least one remote server further performs the steps of providing, via the user interface, an alert that the actual location does not correspond to the assigned location of the mobile workstation where a discrepancy is found during the comparison of the actual location to the assigned location of the mobile workstation.

3. The mobile workstation of claim 1, wherein the second sensor further includes an accelerometer, and wherein the at least one remote server further performs the steps of updating the use state of the mobile workstation to in-transit when the accelerometer detects acceleration of the mobile workstation.

4. The mobile workstation of claim 1, wherein the second sensor further includes an NFC reader, and wherein the at least one remote server further performs the steps of updating the use state of the mobile workstation to at-the-ready when a user having an authorized NFC tag is within operational proximity of the NFC reader.

5. The mobile workstation of claim 1, wherein the wireless network includes a cloud-based system.

6. A method of managing a fleet of mobile workstations in a facility comprising:
   sensing, by a first sensor residing on a mobile workstation of the fleet of mobile work stations, a location of the mobile work station;
   sensing, by a second sensor residing on the mobile workstation, an occurrence of a specified event relating to the use of the mobile workstation;
   transmitting, by a transceiver resident on the mobile workstation and operably coupled to the first sensor, via a wireless network, to a remote server a data packet, wherein the data packet contains data representing the location of the mobile work station and the occurrence of the specified event;
   storing, for the fleet of mobile workstations, use state data when the specified event occurs;
   determining, based on the use state data, a use state of the mobile workstation;
   determining, by the remote server, an actual location and an assigned location to the mobile workstation based on the data packet received by the remote server;
   providing, via a user interface, an option to locate the mobile workstation;
   comparing, by the remote server, the actual location of the mobile workstation to the assigned location of the mobile workstation; and providing, via the user interface, a first notification indicating that the actual location of the mobile workstation corresponds to the assigned location of the mobile workstation.

7. The method of claim 6, further comprising providing, via the user interface, an alert that the actual location does not correspond to the assigned location of the mobile workstation where a discrepancy is found during the comparison of the actual location to the assigned location of the mobile workstation.

8. The method of claim 6, wherein the second sensor includes an accelerometer, and wherein the method further comprises updating, via the remote server further, the use state of the mobile workstation to in-transit when the accelerometer detects acceleration of the mobile workstation.

9. The method of claim 6, wherein the second sensor includes an NFC reader, and wherein the method further comprises updating, via the remote server, the use state of the mobile workstation to at-the-ready when a user having an authorized NFC tag is within operational proximity of the NFC reader.

10. A non-transitory computer readable medium having stored therein instructions that, when executed by a computing device, causes the computing device to perform functions comprising:
   sensing, by a first sensor residing on a mobile workstation, a location of the mobile work station in a fleet of mobile work stations;
   sensing, by a second sensor residing on the mobile workstation, an occurrence of a specified event relating to the use of the mobile workstation;
   storing, for the fleet of mobile workstations, a data packet, wherein the data packet includes an actual location and an assigned location for each mobile workstation in the fleet of mobile workstations, and the occurrence of the specified event;
   providing, via a user interface, an option to locate the mobile workstation;
   comparing, based on the data packet, the actual location of the mobile workstation to the assigned location of the mobile workstation;
   providing, via the user interface, a first notification indicating that the actual location of the mobile workstation, corresponds to the assigned location of the mobile workstation;
   storing, for the fleet of mobile workstations, use state data when the specified event occurs; and
   determining, based on the use state data, a use state of the mobile workstation.

11. The non-transitory computer readable medium of claim 10, the functions further comprising providing, via the user interface, an alert that the actual location does not correspond to the assigned location of the mobile workstation where a discrepancy is found during the comparison of the actual location to the assigned location of the mobile workstation.

12. The non-transitory computer readable medium of claim 10, wherein the second sensor includes an accelerometer, wherein the functions further comprise updating the use state of the mobile workstation to in-transit when the accelerometer detects acceleration of the mobile workstation.

13. The non-transitory computer readable medium of claim 10, wherein the second sensor includes an NFC reader, wherein the functions further comprise updating the use state of the mobile workstation to at-the-ready when a user having an authorized NFC tag is within operational proximity of the NFC reader.

14. The mobile workstation of claim 1, wherein the at least one remote server further performs the step of sending, in response to a selection of the option to locate the mobile workstation, a signal to the mobile workstation which triggers a second notification via the mobile workstation.

15. The method of claim 6, further comprising sending, via the remote server, in response to a selection of the option to locate the mobile workstation, a signal to the mobile workstation which triggers a second notification via the mobile workstation.

16. The method of claim 6, wherein the wireless network includes a cloud-based system.

17. The non-transitory computer readable medium of claim 10, the functions further comprising sending, in response to a selection of the option to locate the mobile workstation, a signal to the mobile workstation which triggers a second notification via the mobile workstation.

18. The non-transitory computer readable medium of claim 10, wherein the wireless network includes a cloud-based system.

* * * * *